`US007790174B2`

(12) United States Patent
Gonthier et al.

(10) Patent No.: US 7,790,174 B2
(45) Date of Patent: Sep. 7, 2010

(54) G-CSF POLYPEPTIDES AND USES THEREOF

(75) Inventors: Catherine Gonthier, Saint Fargeau Ponthierry (FR); Philippe Millasseau, Vayres sur Essonnes (FR)

(73) Assignee: Merck Serono SA, Coinsins, Vaud (CH)

( * ) Notice: Subject to any disclaimer, the term of this patent is extended or adjusted under 35 U.S.C. 154(b) by 263 days.

(21) Appl. No.: 11/722,527

(22) PCT Filed: Dec. 21, 2005

(86) PCT No.: PCT/EP2005/057008

§ 371 (c)(1),
(2), (4) Date: Jun. 22, 2007

(87) PCT Pub. No.: WO2006/067170

PCT Pub. Date: Jun. 29, 2006

(65) Prior Publication Data

US 2008/0145377 A1 Jun. 19, 2008

(30) Foreign Application Priority Data

Dec. 23, 2004 (EP) .................................. 04293107

(51) Int. Cl.
*A61K 39/385* (2006.01)
*A61K 39/00* (2006.01)
*C12N 5/00* (2006.01)
*C12N 15/00* (2006.01)
*C12P 21/06* (2006.01)
*A61K 38/24* (2006.01)
*C07K 1/00* (2006.01)

(52) U.S. Cl. .............................. 424/195.11; 424/192.1; 424/198.1; 435/325; 435/320.1; 435/69.1; 536/23.5; 530/399; 530/351; 530/350

(58) Field of Classification Search ........................ None
See application file for complete search history.

(56) References Cited

U.S. PATENT DOCUMENTS

| 5,399,345 | A | 3/1995 | Schumacher et al. |
| 5,532,341 | A | 7/1996 | Welte et al. |
| 2004/0247562 | A1 | 12/2004 | Lee et al. |

FOREIGN PATENT DOCUMENTS

| EP | 0 243 153 A2 | 4/1987 |
| EP | 1 233 065 A1 | 8/2002 |
| WO | WO 97/12977 A1 | 4/1997 |
| WO | WO 00/40728 A1 | 7/2000 |
| WO | WO 03/018612 A2 | 3/2003 |
| WO | WO 03/027288 A1 | 4/2003 |
| WO | WO2005121174 | * 12/2005 |

OTHER PUBLICATIONS

Dunham et al. 2001. Cytokine 14:347-351.*
Layton et al 2006. Frontiers in Bioscience 11:3181.*
Nagata S. et al. "The chromosomal gene structure and two mRNAs for human granulocyte colony-stimulating factor", *The EMBO Journal*, 1986, pp. 575-581, vol. 5, No. 3.
Souza, L.M. et al. "Recombinant Human Granulocyte Colony-Stimulating Factor: Effects on Normal and Leukemic Myeloid Cells", *Science*, Apr. 4, 1986, pp. 61-65, vol. 232, No. 4746.
Metcalf, D. "The Granulocyte-Macrophage Colony Stimulating Factors", *Cell*, Nov. 1985, pp. 5-6, vol. 43, No. 1.
Swissprot database P09919, Jul. 1, 1989.
Sorg, R. et al. "Rapid and Sensitive mRNA Phenotyping for Interleukins (IL-1 to IL-6) and Colony-stimulating Factors (G-CSF, M-CSF, and GM-CSF) by Reverse Transcription and Subsequent Polymerase Chain Reaction", *Exp. Hematol.*, 1991, pp. 882-887, vol. 19, No. 9.
Cusi, M.G. et al. "Harlequin granulocyte-colony stimulating factor interleukin 6 molecules with bifunctional and antagonistic activities", *Immunotechnology*, Jan. 6, 1997, pp. 61-69, vol. 3, No. 1.
Sarkar, C.A. et al. "Parsing the Effects of Binding, Signaling, and Trafficking on the Mitogenic Potencies of Granulocyte Colony-Stimulating Factor Analogues", *Biotechnol. Prog.*, May-Jun. 2003, pp. 955-964, vol. 19, No. 3.
Hübel, K. et al. "Clinical applications of granulocyte colony-stimulating factor: an update and summary", *Ann Hematol.*, Mar. 6, 2003, pp. 207-213, vol. 82, No. 4.
Gersting, J.A. et al. "Messenger RNA Expression of Granulocyte Colony-Stimulating Factor Receptor Isoforms in the Fetus", *Biology of the Neonate*, 2003, pp. 191-196, vol. 83, No. 3.
Hill, C.P. et al. "The structure of granulocyte-colony-stimulating factor and its relationship to other growth factors", *Proc. Natl. Acad. Sci. USA*, Jun. 1993, pp. 5167-5171, vol. 90.
Seto, Y. et al. "Chromosomal Gene Organization of the Human Granulocyte Colony-Stimulating Factor Receptor", *The Journal of Immunology*, Jan. 1, 1992, pp. 259-266, vol. 148, No. 1.

* cited by examiner

*Primary Examiner*—Gary B. Nickol
*Assistant Examiner*—Shulamith H Shafer
(74) *Attorney, Agent, or Firm*—Saliwanchik, Lloyd & Saliwanchik

(57) ABSTRACT

The present invention relates to G-CSF polypeptides and their uses, particularly for therapeutic or prophylactic treatment in human subjects. The invention also relates to nucleic acids encoding said polypeptides, vectors comprising such nucleic acids and recombinant cells containing the same. The invention further discloses methods of producing such polypeptides, as well as methods and tools for detecting or dosing these polypeptides in any sample.

38 Claims, 4 Drawing Sheets

Figure 1:
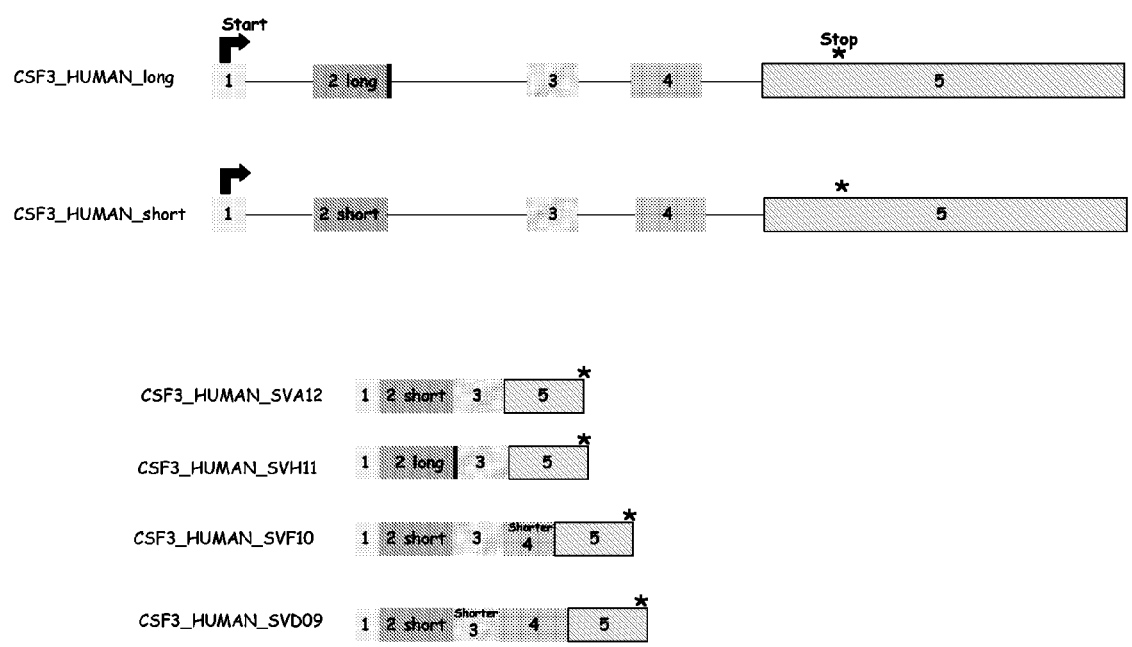

```
                                               Matured protein  Free Cys-17
                       Signal peptide              ↓               ↓         Helix A
CSF3_HUMAN_SVA12      MAGPATQSPMKLMALQLLLWHSALWTVQEA TPLGPASSLPQSFLLKCLEQVRKIQGDGAA
CSF3_HUMAN_SVH11      MAGPATQSPMKLMALQLLLWHSALWTVQEA TPLGPASSLPQSFLLKCLEQVRKIQGDGAA
CSF3_HUMAN_SVF10      MAGPATQSPMKLMALQLLLWHSALWTVQEA TPLGPASSLPQSFLLKCLEQVRKIQGDGAA
CSF3_HUMAN-long       MAGPATQSPMKLMALQLLLWHSALWTVQEA TPLGPASSLPQSFLLKCLEQVRKIQGDGAA
CSF3_HUMAN_short      MAGPATQSPMKLMALQLLLWHSALWTVQEA TPLGPASSLPQSFLLKCLEQVRKIQGDGAA
CSF3_HUMAN_SVD09      MAGPATQSPMKLMALQLLLWHSALWTVQEA TPLGPASSLPQSFLLKCLEQVRKIQGDGAA
                      ********************************************************

Cys-36 Cys-42                  Cys-64     Cys-74
                              ↓    ↓   Helix E              ↓          ↓       Helix B
CSF3_HUMAN_SVA12      LQEKL---CATYKLCHPEELVLLGHSLGIPWAPLSSCPSQALQL---------------
CSF3_HUMAN_SVH11      LQEKLVSECATYKLCHPEELVLLGHSLGIPWAPLSSCPSQALQL---------------
CSF3_HUMAN_SVF10      LQEKL---CATYKLCHPEELVLLGHSLGIPWAPLSSCPSQALQL--------------G
CSF3_HUMAN-long       LQEKLVSECATYKLCHPEELVLLGHSLGIPWAPLSSCPSQALQLAGCLSQLHSGLFLYQG
CSF3_HUMAN_short      LQEKL---CATYKLCHPEELVLLGHSLGIPWAPLSSCPSQALQLAGCLSQLHSGLFLYQG
CSF3_HUMAN_SVD09      LQEKL--------LCHPEELVLLGHSLGIPWAPLSSCPSQALQLAGCLSQLHSGLFLYQG
                      *****        *************************

O-glycosylation site
                                         Helix C                         ↓
CSF3_HUMAN_SVA12      ----------------------------------MEELGMAPALQPTQGAMPAFASAFQRR
CSF3_HUMAN_SVH11      ----------------------------------MEELGMAPALQPTQGAMPAFASAFQRR
CSF3_HUMAN_SVF10      LLQALEGISPELGPTLDTLQLDVADFATTIWQQMEELGMAPALQPTQGAMPAFASAFQRR
CSF3_HUMAN-long       LLQALEGISPELGPTLDTLQLDVADFATTIWQQMEELGMAPALQPTQGAMPAFASAFQRR
CSF3_HUMAN_short      LLQALEGISPELGPTLDTLQLDVADFATTIWQQMEELGMAPALQPTQGAMPAFASAFQRR
CSF3_HUMAN_SVD09      LLQALEGISPELGPTLDALQLDVADFATTIWQQMEELGMAPALQPTQGAMPAFASAFQRR
                                                        ****************************

Helix D
CSF3_HUMAN_SVA12      AGGVLVASHLQSFLEVSYRVLRHLAQP
CSF3_HUMAN_SVH11      AGGVLVASHLQSFLEVSYRVLRHLAQP
CSF3_HUMAN_SVF10      AGGVLVASHLQSFLEVSYRVLRHLAQP
CSF3_HUMAN-long       AGGVLVASHLQSFLEVSYRVLRHLAQP
CSF3_HUMAN_short      AGGVLVASHLQSFLEVSYRVLRHLAQP
CSF3_HUMAN_SVD09      AGGVLVASHLQSFLEVSYRVLRHLAQP
                      ***************************

In bold type: IL6 domain
```

Figure 2

G-CSF POLYPEPTIDES AND USES THEREOF

CROSS-REFERENCE TO RELATED APPLICATION

This application is the U.S. national stage application of International Patent Application No. PCT/EP2005/057008, filed Dec. 21, 2005, the disclosure of which is hereby incorporated by reference in its entirety, including all figures, tables and amino acid or nucleic acid sequences.

The present invention relates to G-CSF polypeptides and their uses, particularly for therapeutic or prophylactic treatment in human subjects. The invention also relates to nucleic acids encoding said polypeptides, vectors comprising such nucleic acids and recombinant cells containing the same, as well as corresponding pharmaceutical compositions. The invention further discloses methods of producing such polypeptides, as well as methods and tools for detecting or dosing these polypeptides in any sample.

BACKGROUND

Granulocyte colony stimulating factor (known also as GCSF, G-CSF, CSF3, or colony stimulating factor-3) is a monomeric secreted protein belonging to the IL-6 protein superfamily. G-CSF acts in hematopoiesis as a cytokine that controls the production, differentiation, and function of granulocytes, a related white cell population of the blood.

The human G-CSF gene contains 5 exons and 4 introns and is located on chromosome 17. Two different polypeptides of molecular weight 19,600 are synthesized from the same gene by differential mRNA splicing (Nagata et al., 1986; Souza et al., 1986; Metcalf, 1985). The two polypeptides differ by the presence (long form) or absence (short form) of 3 amino acids. Expression studies indicate that both the long and short form have G-CSF activity biological activity.

The two forms of G-CSF (designated CSF3_HUMAN) are described in Swissprot databank: one is a polypeptide of 204 amino acids (the "isoform short", P09919-2) and the other is a polypeptide of 207 amino acids (the "isoform long", P09919-1).

G-CSF is a secreted protein; comprising a signal peptide represented by amino acid residues 1 to 30. The resulting matured "short" and "long" isoforms have respectively 174 and 177 amino acids. The mouse orthologue of CSF3_HUMAN is CSF3_MOUSE (Swissprot databank). It is found on mouse chromosome 11. The genomic organization of the mouse gene is similar to that of the human with 5 exons and 4 introns. No alternatively spliced forms have been reported for the mouse gene.

G-CSF has two intra-molecular disulfide linkages between Cys-36 and Cys-42, and between Cys-64 and Cys-74, with a free cysteine residue at position 17. It also contains an O-glycosylation site at Thr-133 (all numbering is done with respect to the mature (lacking the signal peptide) short form of the polypeptide). The protein can be glycosylated with O-glycan consisting of Gal-GalNAc disaccharide, which can be modified with up to two sialic acid residues (done in recombinantly expressed G-CSF from CHO cells).

The secondary structure of human G-CSF is dominated by alpha-helical regions with four stretches of helices. The four stretches of helices have been identified between residues 11 and 41 (helix A), 71 and 95 (helix B), 102 and 125 (helix C), and 145 and 170 (helix D), which form a left-handed four-helix bundle with helices A and B aligned parallel to one another (up-up) and antiparallel to helices C and D (down-down). An additional short fifth helix (E) is part of the AB loop connecting helices A and B.

hG-CSF and related mutants or variants cDNAs and proteins have been disclosed in EP0243153. Splicing variants of G-CSF have been reported in R. Sorg, J. Enczmann, U. Sorg, K. Heermeier, E. M. Schneider, and P. Wernet. Rapid and sensitive mRNA phenotyping for interleukins (IL-1 to IL-6) and colony-stimulating factors (G-CSF, M-CSF, and GM-CSF) by reverse transcription and subsequent polymerase chain reaction. *Exp Hematol JID*—0402313 19 (9):882-887, 1991; Cusi M. Grazia and D. Ferrero. Harlequin granulocyte-colony stimulating factor interleukin 6 molecules with bifunctional and antagonistic activities. *Immunotechnology JID*—9511979 3 (1):61-69, 1997; and WO03027288A1. Analogs of human G-CSF have been generated by mutagenesis or by fusion with heterologous sequences immunogenicity half-life (WO 04/020576; WO 02/020767; WO 02/020766; WO02/066514; WO 02/077034; WO 03/076567; WO 02/069232; WO 01/073081; WO 99/58662; WO 96/39422; WO 95/21254; WO 95/13393; WO 95/33057; WO 92/06116; WO 90/12874; EP272703; EP459630; EP243153; U.S. Pat. No. 4,904,584; U.S. Pat. No. 4,810,643; AU 76380/91; AU 10948/92). Also, non-natural variants of human G-CSF have been generated to improve their activity by mutagenizing specific residues and linking non-peptide moieties such as PEG molecules (WO 03/031464; WO 03/006501; EP401384; EP473268; EP335423; U.S. Pat. No. 5,824,778; U.S. Pat. No. 5,824,784). Furthermore, antibodies against human G-CSF have been described (EP0331186).

G-CSF activates a receptor of the hematopoietin receptor superfamily, the G-CSF receptor (G-CSF-R), which subsequently triggers multiple signalling mechanisms. Four isoforms of G-CSF-R are described in Swissprot (Accession no Q99062), but seven human G-CSF-R isoforms seem to exist, all generated by alternative splicing of a single receptor gene transcript. Some of the isoforms of G-CSF-R seem to have tissue specificity.

The G-CSF-R forms a tetrameric complex with G-CSF, said complex comprising two ligand and two receptor molecules. The $NH_2$ region (residues 20-46) and the COOH terminal region (including helix D) of G-CSF are involved in binding to the receptor. Different studies agreed with the presence of one receptor-binding site involving various residues on the helices A and C. Some reports suggested the existence of a second binding site located on the helix E (1997, PMID 9194183; 2003, PMID 12946100). The most important residue for receptor binding is Glu 19 (in helix A). Other quoted residues are Lys 40, Glu 46 (helix E) and Phe 144 (helix D). In addition to these residues, Val 48, Leu 49 (helix E), Leu 15 (helix A), Asp 112 and Leu 124 (helix C) seem to be important for biological activity.

G-CSF is available as a drug under different names (Neupogen, Granulokine, or Granocyte) for the treatment of neutropenia, a disorder characterized by an extremely low number of neutrophils in blood, as an adjunct to chemotherapy, bone marrow transplantation, and collection of CSF-mobilised peripherical blood progenitors cells.

The efficacy of G-CSF in decreasing the risk of infections in Felty's syndrome and systemic lupus erythematosus (SLE) has also been well documented (Chronic neutropenia with autoimmune diseases is associated mainly with rheumatoid arthritis as Felty's syndrome or large granular leukaemia, and with SLE).

The use of G-CSF for the treatment of myelogenous leukemia has been described in EP0231819.

G-CSF also provides therapeutic effect in fighting infections, by causing selective activation of distinct early response genes through different JAK-STAT signalling molecules.

G-CSF has also been described as having anti-apoptotic activity through protein synthesis-dependent mechanisms involving the Janus kinase-STAT pathway.

G-CSF also finds therapeutic utility in clinical transplantation, since this protein induces the mobilization of hematopoietic progenitor stem cells (HPCs) (HPCs ensure the continuous renewal of mature blood cells). In this respect, Petit et al. (2002) investigated the mobilization of hematopoietic progenitor stem cells (HPCs) induced by GCSF. ELISA and immunohistologic analysis showed a significant reduction in SDF1 (CXCL12; 600835) in human and mouse bone marrow plasma and immature osteoblasts, but not peripheral blood, within 24 hours of GCSF treatment. Manipulation of SDF1-CXCR4 interactions may be an improved way to control the navigation of progenitor cells between the bone marrow and blood.

Levesque et al. (2003) demonstrated that the mobilization of HPCs by granulocyte colony-stimulating factor or cyclophosphamide was due to the disruption of the CXCR4/CXCL12 chemotactic pathway. The mobilization of HPCs coincided in vivo with the cleavage of the N terminus of the chemokine receptor CXCR4 found on HPCs. This resulted in the loss of chemotactic response of the HPCs to the CXCR4 ligand, CXCL12. The concentration of CXCL12 was also decreased in vivo in the bone marrow of mobilized mice, and this decrease coincided with the accumulation of serine proteases capable of direct cleavage and inactivation of CXCL12. As both CXCL12 and CXCR4 are essential for the homing and retention of HPCs in the bone marrow, the proteolytic degradation of CXCL12 and CXCR4 may represent a critical step in the mobilization of HPCs into the peripheral blood by GCSF or cyclophosphamide.

G-CSF has also been associated with the expression of proliferation vascularization in meningioma.

Moreover, a significantly higher level of G-CSF has been found in follicular fluid than in serum. Combined with the fact that G-CSF and its receptor are expressed in follicular fluid by granulosa cells, it has been suggested that G-CSF plays an important role in ovarian function. Other results demonstrate that G-CSF is produced in the human follicle shortly before the ovulatory phase and may play a role in the mechanism of ovulation.

G-CSF also seems to have immunomodulatory function in host defence. G-CSF administration has a number of effects that might simultaneously enhance host defence while reducing the risk of developing uncontrolled systemic inflammation. This may also be efficacious in prolonging graft survival and reducing graft versus host disease. Significant associations of endogenous G-CSF levels with anti-inflammatory mediators early in the development of severe lung injury suggest an endogenous anti-inflammatory role of G-CSF in vivo.

Recombinant G-CSF induces production of anti-inflammatory factors and is protective against endotoxin- and sepsis-induced organ injury. It has been suggested that rG-CSF may be beneficial as an adjunct therapy for treatment of serious bacterial and opportunistic fungal infections in normeutropenic patients, including those with alterations in neutrophil function. Endogenous G-CSF increases neutrophil function in patients with severe sepsis and septic shock, necessary for resolution of bacterial infections in these patients (2002, PMID 12027409).

It has been reported that G-CSF improves cardiac function and reduces mortality after acute myocardial infarction (Myocardial infarction is accompanied with an inflammatory reaction which induces cardiac dysfunction and remodelling). Takano et al (2003, PMID 12769752) suggested that G-CSF may regenerate cardiac myocytes and blood vessels through mobilization of bone marrow stem cells.

Recombinant G-CSF induces production of anti-inflammatory factors and is protective against endotoxin- and sepsis-induced organ injury (Root et al., 1999). Hartung (1999, PMID 10596675) indicated that, in addition to its anti-infectious role, G-CSF has an immunomodulatory function and also augments antibiotic efficacy. Important uses of G-CSF in oncology are prevention of febrile neutropenia after chemotherapy, treatment of febrile neutropenic episodes and support following bone marrow transplantation, and collection of CSF-mobilised peripherical blood progenitors cells (Dale, 2002, PMID 12479591).

Considering the biological activities of G-CSF, it would be highly valuable to obtain biologically active G-CSF variants, particularly agonists of human G-CSF.

SUMMARY OF THE PRESENT INVENTION

The present invention discloses novel G-CSF polypeptides and their uses, particularly for therapeutic or prophylactic treatment in human subjects. The invention also discloses nucleic acids encoding said polypeptides, vectors comprising such nucleic acids, in particular expression vectors, and recombinant cells containing the same, as well as corresponding pharmaceutical compositions. The invention further discloses methods of producing such polypeptides, as well as methods and tools for detecting or dosing these polypeptides in any sample. Further included are antibodies specific for the novel G-CSF variants of the present invention.

More particularly, the present invention results from the identification, isolation and characterization of novel splicing variants of G-CSF having particular structural and biological properties, which represent valuable pharmaceutical products.

An object of this invention thus resides in isolated human G-CSF polypeptide variants, or a distinctive fragment thereof. The polypeptide variants of this invention comprise the sequence of a mature human G-CSF polypeptide, but lacking at least five consecutive amino acids, and wherein only one of these amino acids is a disulfide bridge forming cystein residue.

Another object of this invention resides in a fusion protein comprising a human G-CSF polypeptide variant as defined above, or a conjugate thereof.

A further object of this invention resides in a nucleic acid encoding a human G-CSF polypeptide variant or a fusion protein as defined above, as well as any cloning or expression vector comprising such a nucleic acid.

The invention also relates to recombinant host cells comprising a vector or nucleic acid as defined above, as well as to methods of producing a human G-CSF polypeptide variant as defined above using such recombinant cells.

A further aspect of this invention resides in a pharmaceutical composition comprising a polypeptide, nucleic acid, vector or recombinant cell as defined above.

A further aspect of this invention resides in the use of a polypeptide, nucleic acid, vector or recombinant cell as defined above, for the manufacture of a pharmaceutical composition for use in a human subject.

The above products and pharmaceutical composition are particularly suited, for instance, for stimulating the immune system in a subject, for treating cancers, infectious diseases, or cardiopathologies, to support organ transplant, to treat inflammatory diseases or to inhibit apoptosis.

A further object of this invention also relates to an antibody, or a fragment or derivative of such an antibody, that selectively binds a polypeptide as defined above.

A further aspect of this invention resides in a method of detecting or dosing a polypeptide as defined above in a sample, e.g., using an antibody, fragment or derivative thereof as defined above.

Other aspects of this invention include primers and probes specific for a nucleic acid as defined above, as well as their uses to detect or diagnose the presence of such a nucleic acid in a sample.

LEGEND TO THE FIGURES

FIG. 1: Schematic representation of splicing events leading to variants of this invention.

FIG. 2: Sequence alignments between mature G-CSF and G-CSF variants of this invention using Clustal W (1.83) (CSF3_HUMAN_SVA12, SEQ ID NO:4; CSF3_HUMAN_SV11, SEQ ID NO: 6; CSF3_HUMAN_SVF10, SEQ ID NO: 2; CSF3_HUMAN_long, SEQ ID NO: 9: CSF3_HUMAN_short, SEQ ID NO: 10; CSF3_HUMAN_SVD09, SEQ ID NO: 8).

Figure 3:
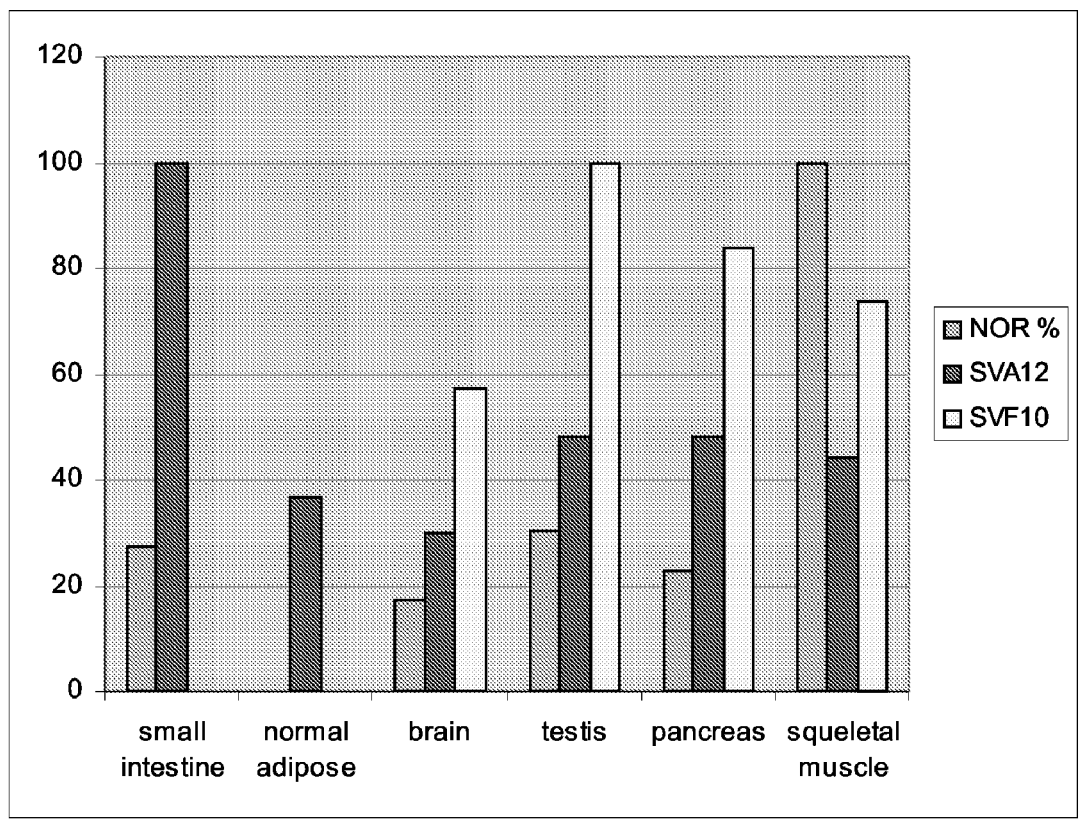

FIG. 3: Tissue expression of G-CSF variants SVA12 and SVF10.

Figure 4:
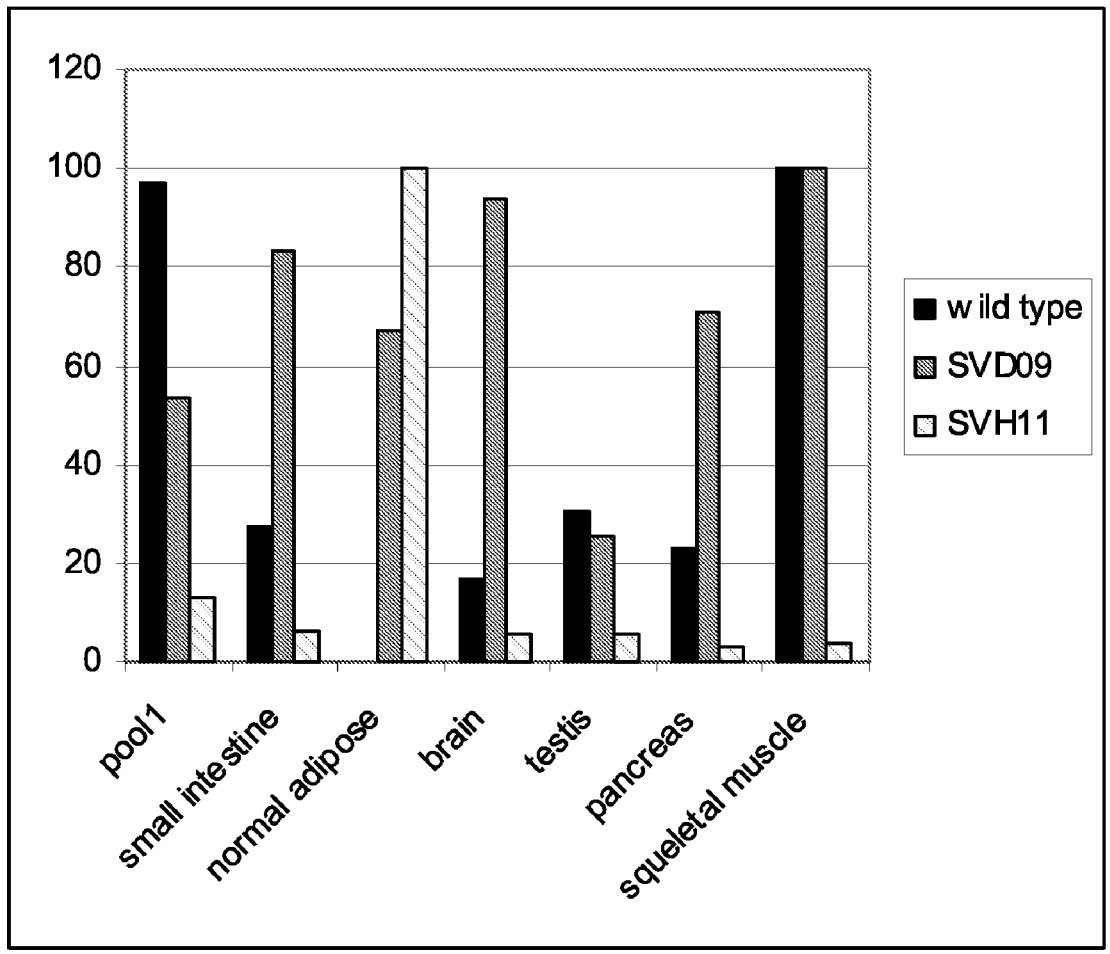

FIG. 4: Tissue expression of G-CSF variants SVD09 and SVH11.

DETAILED DESCRIPTION OF THE INVENTION

The present invention results from the identification and characterization of novel biologically active human G-CSF polypeptides. These polypeptides more specifically comprise the sequence of a mature human G-CSF polypeptide, but lacking at least five consecutive amino acids, and wherein only one of these amino acids is a disulfide bridge forming cystein residue. Further included in the present invention are distinctive fragments thereof, which retain the biological activity of G-CSF. The polypeptides of the present invention may be naturally occurring or synthetic G-CSF variant polypeptides as polypeptides provided herein, and represent valuable therapeutic molecules.

As described above and found in the prior art, G-CSF exists as two isoforms, one of which contains 207 amino acids ("long isoform") and one which contains 204 amino acids ("short isoform"). The difference between the two isoforms is that the shorter has three amino acids missing from the end of the second exon. Each isoform contains an N-terminal signal peptide consisting of amino acids numbered 1 to 30. Within the context of the present invention, what is meant by "mature G-CSF polypeptide" is a human G-CSF polypeptide lacking the N-terminal signal peptide. Exemplary amino acid sequences of a mature human G-CSF polypeptide are represented in SEQ ID NOs: 9 (long form) and 10 (short form). The polypeptide may be glycosylated or not.

The term "isolated" indicates that the polypeptides or nucleic acids of this invention are not in their natural environment. Isolated products of this invention may thus be contained in a culture supernatant, partially enriched or purified, produced from heterologous sources, cloned in a vector or formulated with a vehicle, etc.

As disclosed above, the polypeptide variants of this invention comprise the sequence of a mature human G-CSF polypeptide, but lack at least five consecutive amino acids, wherein only one of these amino acids is a disulfide bridge forming cystein residue. Mature human G-CSF, as described herein and found in the prior art, comprises 5 cystein residues, located at position 17, 36, 42, 64 and 74. Cys36 and Cys42, as well as Cys64 and Cys74 each form disulfide bonds, while Cys17 is a free cystein residue, which is not naturally involved in disulfide linkage. Accordingly, within the context of this invention, a disulfide bridge forming cystein residue designates any one of the following cystein residues: Cys36, Cys42, Cys64 or Cys74.

G-CSF polypeptide variants of this invention specifically lack at least one stretch of 5 amino acid residues as compared to mature human G-CSF, said stretch containing one cystein residue selected from Cys36, Cys42, Cys64 or Cys74. More preferably, the disulfide bridge forming cystein residue is Cys 36 or Cys74. The G-CSF polypeptide variants of this invention lack a stretch of consecutive amino acid residues containing from 5 up to about 60 amino acid residues, more preferably up to about 55 amino acid residues, even more preferably up to about 50 amino acid residues. Specific examples of G-CSF variants of this invention lack amino acid residues 36-40, 72-86 or 72-120, as compared to the mature, long or short G-CSF isoform.

The following specific G-CSF variants according to the present invention have been purified and characterized and designated as CSF3-SVF10, CSF3-SVA12, CSF3-SVH11 and CSF3-SVD09:

Splicing variant CSF3-SVF10, contains 5 exons (FIG. 1). The nucleotide and amino acid sequences of this variant are depicted in SEQ ID NO:1 and 2, respectively. This polypeptide corresponds to a variant of the short isoform of CSF3. The fourth exon of this variant is shorter at the 5' end, the effect of which is the absence of amino acid residues numbered 72-86. CSF3-SVF10 thus lacks part of helix B and one cystein residue (Cys-74) involved in one disulfide linkage. This variant retains helices A and C, which are involved in binding to the G-CSF receptor, as well an IL6 domain.

Splicing variant CSF3-SVA12, contains 4 exons (FIG. 1). The nucleotide and amino acid sequences of this variant are depicted in SEQ ID NOs: 3 and 4, respectively. This polypeptide also corresponds to a variant of the short isoform of CSF3. In this variant, the fourth exon of CSF3-SVA12 is smaller, the effect of which is the absence of amino acid residues numbered 72-120). CSF3-SVF12 thus lacks helix B, part of helix C, and one cystein residue (Cys-74) involved in one disulfide linkage. This variant retains helix A which is involved in binding to the G-CSF receptor, as well an IL6 domain.

Splicing variant CSF3-SVH11, contains 4 exons (FIG. 1). The nucleotide and amino acid sequences of this variant are depicted in SEQ ID NO:5 and 6, respectively. This polypeptide corresponds to a variant of the long isoform of CSF3. In this variant, the fourth exon of CSF3-SVH11 is smaller the effect of which is the absence of amino acid residues 72-120. CSF3-SVH11 thus lacks helix B, part of helix C, and one cystein residue, Cys-74, involved in one disulfide linkage. This variant retains helix A which is involved in binding to the G-CSF receptor, as well an IL6 domain.

Splicing variant CSF3-SVD09, contains 5 exons (FIG. 1). The nucleotide and amino acid sequences of this variant are depicted in SEQ ID NO:7 and 8, respectively. This polypeptide corresponds to a variant of the short isoform of CSF3 because. The third exon of this variant is shorter at the 5' end, the effect of which is the absence of amino acidresidues 36-40). CSF3-SVD09 thus lacks one cystein residue Cys-36 involved in one disulfide linkage. This variant retains helices A and C which are involved in binding to the G-CSF receptor, as well an IL6 domain. It also contains one polymorphism, T138A.

A particular embodiment of this invention resides in an isolated human G-CSF polypeptide which is or comprises SEQ ID NO: 2 [CSF3-SVF10].

Another particular embodiment of this invention resides in an isolated human G-CSF polypeptide which is or comprises SEQ ID NO: 4 [CSF3-SVH11] or SEQ ID NO: 6 [CSF3-SVA12].

A further particular embodiment of this invention resides in an isolated human G-CSF polypeptide which is or comprises SEQ ID NO: 8 [CSF3-SVD09].

The present invention also includes any polypeptide comprising a distinctive fragment of a G-CSF polypeptide variant as disclosed above. Within the context of this invention, a distinctive fragment designates a fragment of at least 5 consecutive amino acids that comprises the sequence formed as a result of the absence of amino acid residues as set forth above for G-CSF variants of the present invention. In particular, said sequence shall comprise two consecutive amino acid residues that are not so linked in a mature G-CSF polypeptide, but are brought together by the absence of intervening amino acid residues as described herein. Such a distinctive fragment may comprise up to 10, 20, 30, 40, 50 or more consecutive amino acid residues of the variant, as long as it comprises the above described consecutive amino acid residues.

In this regard, a particular object of this invention resides in a human G-CSF polypeptide variant, wherein said polypeptide variant comprises an amino acid motif selected from LQLME (amino acid residues 99-103 of SEQ ID NO: 4 (SVA12)), LQLGL (amino acid residues 99:103 of SEQ ID NO: 2 (SVF10)), and EKLLC (amino acid residues 63-67 of SEQ ID NO: 8 (SVD09)).

In addition to the above, the human G-CSF polypeptide variants of this invention may further comprises one or several amino acid substitutions as compared to the mature G-CSF polypeptide, typically from 0 to 10 amino acid substitutions, even more typically from 0 to 5, 4, 3, 2 or 1 amino acid substitutions. Such substitutions more preferably affect one cystein residue, in particular cystein residue in position 17, 42 or 64, which may be replaced by distinct amino acid residues. Examples of cystein-replacing amino acid residues include, without limitation, Serine and Threonine.

Also, in a particular embodiment, the above polypeptide variants of the present invention may comprise additional amino acid residues. In particular, the invention encompasses the above-disclosed variants in which the lacking disulfide bridge forming cystein residue is reintroduced into the polypeptide sequence, within a different amino acid context, at the same distance from the remaining bridging cystein residue. As an example, the invention encompasses G-CSF polypeptide variants comprising the following amino acid sequences: CPSQALQLMEC (SEQ ID NO: 11), CPSQALQLGLC (SEQ ID NO: 12) or CQEKLLC (SEQ ID NO: 13).

Preferred human G-CSF polypeptides of this invention are biologically active, i.e., bind to a G-CSF receptor and retain an IL-6 domain. Helix A is employed by the G-CSF known in the art in binding its receptor. In particular, the biologically active polypeptides of this invention modulate the production, differentiation, and/or function of granulocytes.

Preferred human G-CSF polypeptides of this invention retain at least one of the following biological activities:
  ability to increase the number of granulocytes in the blood stream, in particular neutrophilic granulocytes; ability to increase the production of granulocytes; ability to increase the differentiation of granulocytes; ability to improve the function of granulocytes
  ability to mobilize of hematopoietic progenitor stem cells (HPCs)
  anti-apoptotic activity, preferably anti-apoptotic activity through protein synthesis-dependent mechanisms involving the Janus kinase-STAT pathway
  ability to induce the production of anti-inflammatory factors In particular, preferred human G-CSF polypeptides of this invention show activity in the Assay 1 according to Example D, measuring the mobilization of hematopoietic progenitor cells from the bone marrow. Furthermore, preferred human G-CSF polypeptides of this invention may show activity in the Assay 2 according to Example D, measuring anti-inflammatory activity.

Preferred human G-CSF polypeptides of this invention are useful in at least one of the following medical indications:
  the treatment of neutropenia
  the treatment of inflammation, in particular the treatment of inflammations of the intestine, in particular the treatment of inflammations of the small intestine, the treatment of Crohn's disease, the treatment of colitis ulcerosa
  the prevention of infections, in particular the prevention of infections in Felty's syndrome and systemic lupus erythematosus (SLE)
  the treatment cancer, in particular of myelogenous leukemia
  the increase of ovarian function
  the improvement cardiac function
  the protection against endotoxin- and sepsis-induced organ injury
  the treatment of adipose-related disorders, such as for example obesity and diabetes The present invention also relates to fusion proteins comprising a G-CSF polypeptide variant as disclosed above, operably linked to an additional amino acid domain. The additional amino acid domain may be located upstream (N-ter) or downstream (C-ter) from the sequence of the G-CSF polypeptide variant. The additional domain may comprise any functional region, providing for instance an increased stability, targeting or bioavailability of the fusion protein; facilitating purification or production, or conferring on the molecule additional biological activity. Specific examples of such additional amino acid sequences include a GST sequence, a His tag sequence, a multimerication domain, the constant region of an immunoglobulin molecule or a heterodimeric protein hormone such as human chorionic gonadotropin (hCG) as described in U.S. Pat. No. 6,193,972. The term "operably linked" indicates that the polypeptide and additional amino acid domain are associated through peptide linkage, either directly or via spacer residues. In this manner, the fusion protein can be produced recombinantly, by direct expression in a host cell of a nucleic acid molecule encoding the same, as will be discussed below. Also, if needed, the additional amino acid sequence included in the fusion proteins may be eliminated, either at the end of the production/purification process or in vivo, e.g., by means of an appropriate endo-/exopeptidase. For example, a spacer sequence included in the fusion protein may comprise a recognition site for an endopeptidase (such as a caspase) that can be used to separate by enzymatic cleavage the desired polypeptide variant from the additional amino acid domain, either in vivo or in vitro.

In a particular embodiment, the additional amino acid residues in the fusion protein comprise an amino acid sequence derived from the constant region of an immunoglobulin, particularly the Fc portion of a human immunoglobulin. The sequence of the Fc portion may be derived for instance from an IgG, preferably from a human IgG. Said Ig sequence may also be modified to reduce effector function or to increase the stability of a resulting dimmer. The amino acid sequence derived from the constant region of an immunoglobulin may be linked to the C-terminus or to the N-terminus of the G-CSF polypeptide variant, preferably to the C-terminus.

In a further particular embodiment, the additional amino acid residues in the fusion protein comprise a multimerization domain, allowing complexes to be formed between two or more fusion proteins of this invention, or between one or more fusion proteins of this invention and a distinct protein. An example of such multimerization domains include a leucine zipper. The multimerization domain may be linked to the C-terminus or to the N-terminus of the G-CSF polypeptide variant, preferably to the C-terminus.

The present invention also relates to G-CSF variants as disclosed herein containing a signal peptide, along with the corresponding DNA sequence encoding such variants. The signal peptide may be the naturally occurring signal peptide as disclosed herein for the long or short isoforms of G-CSF, or may be a heterolous or synthetic signal peptide.

The present invention also relates to the above-disclosed G-CSF polypeptide variants comprising an additional N-terminal amino acid residue. Indeed, depending on the expression system and conditions, polypeptides of the invention may be expressed in a recombinant host cell with a starting Methionine. This additional amino acid may then be either maintained in the resulting recombinant protein, or eliminated by means of an exopeptidase, such as Methionine Aminopeptidase, according to methods disclosed in the literature (Van Valkenburgh H A and Kahn R A, 2002; Ben-Bassat A, 1991).

The polypeptides or fusion proteins of the invention can be in the form of active conjugates or complex with a molecule, which may be selected from radioactive labels, biotin, fluorescent labels, cytotoxic agents, drug delivery agents, and the like. Useful conjugates or complexes can be generated using molecules and methods known per se in the art, for example for allowing the detection of the interaction with the G-CSF receptor (radioactive or fluorescent labels, biotin), therapeutic efficacy (cytotoxic agents), or improving the agents in terms of drug delivery efficacy, such as polyethylene glycol and other natural or synthetic polymers (Harris J M and Chess R B, 2003; Greenwald R B et al., 2003; Pillai O and Panchagnula R, 2001).

Polypeptides and fusion proteins of this invention may be produced by any technique known per se in the art, such as by recombinant technologies, chemical synthesis, cloning, ligations, or combinations thereof.

In a particular embodiment, the polypeptides or fusion proteins are produced by recombinant technologies, e.g., by expression of a corresponding nucleic acid in a suitable host cell.

In this regard, the term "nucleic acid molecule" encompasses all different types of nucleic acids, including without limitation deoxyribonucleic acids (e.g., DNA, cDNA, gDNA, synthetic DNA, etc.), ribonucleic acids (e.g., RNA, mRNA, etc.) and peptide nucleic acids (PNA). In a preferred embodiment, the nucleic acid molecule is a DNA molecule, such as a double-stranded DNA molecule or a cDNA molecule. A particular object of this invention resides more specifically in a nucleic acid molecule that comprises a nucleotide sequence selected from SEQ ID NOs: 1, 3, 5 and 7, or a complementary strand or degenerate sequence thereof.

A degenerate sequence designates any nucleotide sequence encoding the same amino acid sequence as a reference nucleotide sequence, but comprising a distinct nucleotide sequence as a result of the genetic code degeneracy.

A further object of this invention is a vector comprising a nucleic acid molecule as defined above. The vector may be any cloning or expression vector, integrative or autonomously replicating, functional in any prokaryotic or eukaryotic cell. In particular, the vector may be a plasmid, cosmid, virus, phage, episome, artificial chromosome, and the like. The vector may comprise regulatory elements, such as a promoter, terminator, enhancer, selection marker, origin of replication, etc. Specific examples of such vectors include prokaryotic plasmids, such as pBR, pUC or pcDNA plasmids; viral vectors, including retroviral, adenoviral or AAV vectors; bacteriophages; baculoviruses; BAC or YAC, etc., as will be discussed below A further aspect of this invention is a recombinant host cell, wherein said cell comprises a nucleic acid molecule or a vector as defined above. The host cell may be a prokaryotic or eukaryotic cell. Examples of prokaryotic cells include bacteria, such as *E. coli*. Examples of eukaryotic cells are yeast cells, plant cells, mammalian cells and insect cells including any primary cell culture or established cell line (e.g., 3T3, Véro, HEK293, TN5, etc.). Particularly preferred mammalian cells of the present invention are CHO cells.

Another object of this invention is a method of producing a G-CSF variant polypeptide as described herein, the method comprising culturing a recombinant host cell of the invention under conditions allowing expression of the nucleic acid molecule, and recovering the polypeptide produced. The polypeptide produced may be glycosylated or not, or contain other post-translational modifications depending on the host cell type used.

Many books and reviews provide teachings on how to clone and produce recombinant proteins using vectors and prokaryotic or eukaryotic host cells, such as some titles in the series "A Practical Approach" published by Oxford University Press ("DNA Cloning 2: Expression Systems", 1995; "DNA Cloning 4: Mammalian Systems", 1996; "Protein Expression", 1999; "Protein Purification Techniques", 2001).

In general, the vectors can be episomal or non-/homologously integrating vectors, which can be introduced into the appropriate host cells by any suitable means (transformation, transfection, conjugation, protoplast fusion, electroporation, calcium phosphate-precipitation, direct microinjection, etc.). Factors of importance in selecting a particular plasmid, viral or retroviral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. The vectors should allow the expression of the polypeptide or fusion proteins of the invention in prokaryotic or eukaryotic host cells, under the control of appropriate transcriptional initiation/termination regulatory sequences, which are chosen to be constitutively active or inducible in said cell. A cell line substantially enriched in such cells can be then isolated to provide a stable cell line.

For eukaryotic host cells (e.g. yeasts, insect or mammalian cells), different transcriptional and translational regulatory sequences may be employed, depending on the nature of the host. They may be derived form viral sources, such as adenovirus, papilloma virus, Simian virus or the like, where the regulatory signals are associated with a particular gene which has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated. The cells which have been stably transformed by the introduced DNA can be selected by also introducing one or more markers which allow for selection of host cells which contain the expression vector. The marker may also provide for phototrophy to an auxotrophic host, biocide resistance, e.g. antibiotics, or heavy metals such as copper, or the like. The selectable marker gene can be either directly linked to the DNA sequences to be expressed (e.g., on the same vector), or introduced into the same cell by co-transfection. Additional elements may also be needed for optimal synthesis of proteins of the invention.

Particularly suitable prokaryotic cells include bacteria (such as *Bacillus subtilis* or *E. coli*) transformed with a recombinant bacteriophage, plasmid or cosmid DNA expression vector. Such cells typically produce proteins comprising a N-terminal Methionine residue, such proteins representing particular objects of this invention. Preferred cells to be used in the present invention are eukaryotic host cells, e.g. mammalian cells, such as human, monkey, mouse, and Chinese Hamster Ovary (CHO) cells, because they provide post-translational modifications to protein molecules, including correct folding or glycosylation at correct sites. Alternative eukaryotic host cells are yeast cells (e.g., *Saccharomyces, Kluyveromyces*, etc.) transformed with yeast expression vectors. Also yeast cells can carry out post-translational peptide modifications including glycosylation. A number of recombinant DNA strategies exist which utilize strong promoter sequences and high copy number of plasmids that can be utilized for production of the desired proteins in yeast. Yeast cells recognize leader sequences in cloned mammalian gene products and secrete polypeptides bearing leader sequences (i.e., pre-peptides).

For long-term, high-yield production of a recombinant polypeptide, stable expression is preferred. For example, cell lines which stably express the polypeptide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type. A cell line substantially enriched in such cells can be then isolated to provide a stable cell line.

A particularly preferred method of high-yield production of a recombinant polypeptide of the present invention is through the use of dihydrofolate reductase (DHFR) amplification in DHFR-deficient CHO cells, by the use of successively increasing levels of methotrexate as described in U.S. Pat. No. 4,889,803. The polypeptide obtained may be in a glycosylated form.

Mammalian cell lines available as hosts for expression are known in the art and include many immortalised cell lines available from the American Type Culture Collection (ATCC) including, but not limited to, Chinese hamster ovary (CHO), HeLa, baby hamster kidney (BHK), monkey kidney (COS), C127, 3T3, BHK, HEK 293, Bowes melanoma and human hepatocellular carcinoma (for example Hep G2) cells and a number of other cell lines. In the baculovirus system, the materials for baculovirus/insect cell expression systems are commercially available in kit form from, inter alia, Invitrogen.

In addition to recombinant DNA technologies, the polypeptides or fusion proteins of this invention may be prepared by chemical synthesis technologies. Examples of chemical synthesis technologies are solid phase synthesis and liquid phase synthesis. As a solid phase synthesis, for example, the amino acid corresponding to the carboxy-terminus of the polypeptide to be synthesised is bound to a support which is insoluble in organic solvents and, by alternate repetition of reactions (e.g., by sequential condensation of amino acids with their amino groups and side chain functional groups protected with appropriate protective groups), the polypeptide chain is extended. Solid phase synthesis methods are largely classified by the tBoc method and the Fmoc method, depending on the type of protective group used. Totally synthetic proteins of size comparable to that of G-CSF are disclosed in the literature (Brown A et al., 1996).

The polypeptides of the present invention can be produced, formulated, administered, or generically used in other alternative forms that can be preferred according to the desired method of use and/or production. The proteins of the invention can be post-translationally modified, for example by glycosylation. The polypeptides or proteins of the invention can be provided in isolated (or purified) active form, or as precursors, derivatives and/or salts thereof.

As indicated above, the term "active" or "biologically active" means that such polypeptides have the capacity to bind to a G-CSF receptor and/or contain an IL-6 domain and furthermore are able to score positively in assays for G-CSF activity that are well known in the art. Non-limiting examples of such assays are exemplified below.

"Precursors" are compounds which can be converted into the polypeptides of present invention by metabolic and/or enzymatic processing prior to or after administration thereof to cells or an organism.

The term "salts" herein refers to both salts of carboxyl groups and to acid addition salts of amino groups of the polypeptides of the present invention. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid. Any of such salts should have substantially similar activity to the polypeptides of the invention.

The term "derivatives" as used herein refers to derivatives that can be prepared from the functional groups present on the lateral chains of the amino acid moieties or on the amino-/or carboxy-terminal groups according to methods known per se in the art. Such derivatives include for example esters or aliphatic amides of the carboxyl-groups and N-acyl derivatives of free amino groups or O-acyl derivatives of free hydroxyl-groups and are formed with acyl-groups as for example alcanoyl- or aroyl-groups.

Purification of the polypeptides of the invention can be carried out by a variety of methods known per se in the art, such as, without limitation, any conventional procedure involving extraction, precipitation, chromatography, electrophoresis, or the like. A particular purification procedure is affinity chromatography, using (monoclonal) antibodies or affinity groups which selectively bind the polypeptide and which are typically immobilized on a gel matrix contained within a column. Purified preparations of the proteins of the invention, as used herein, refers to preparations which contain less than 15% of contaminants, more preferably which comprise at least 90, 95 or 97% of the polypeptide.

A further object of this invention is a pharmaceutical composition comprising a polypeptide or protein, a nucleic acid molecule, a vector or a cell as defined above, and a pharmaceutically acceptable carrier or diluent. More preferred pharmaceutical compositions of this invention comprise a polypeptide variant comprising SEQ ID NO: 2, 4, 6 or 8, or a fusion protein comprising such variant.

Another aspect of this invention relates to the use of a polypeptide or protein, nucleic acid molecule, vector or cell as disclosed above, for the manufacture of a pharmaceutical composition for treating a human subject.

In general, given the involvement of G-CSF in many human and veterinary disorders, the products of the invention can used for treating or preventing various pathological conditions, such as immune disorders, cancers, infectious diseases, inflammatory diseases, to support organ transplant, or the like.

In a particular embodiment, the invention relates to products or compositions as defined above for stimulating the immune system in a subject, particularly for controlling the production, differentiation and/or function of granulocytes.

In another particular embodiment, the invention relates to products or compositions as defined above for treating cancer in a subject, particularly for stimulating the immune system of subjects having a cancer.

In another particular embodiment, the invention relates to products or compositions as defined above for treating an inflammatory disease in a subject.

In another particular embodiment, the invention relates to products or compositions as defined above for treating an infectious disease in a subject.

The pharmaceutical compositions may contain, in combination with the polypeptides or proteins of the invention as active ingredient, suitable pharmaceutically acceptable diluents, carriers, biologically compatible vehicles and additives which are suitable for administration to an animal (for example, physiological saline solution) and optionally comprising auxiliaries (like excipients, stabilizers, or adjuvants) which facilitate the processing of the active compounds into preparations which can be used pharmaceutically. The pharmaceutical compositions may be formulated in any acceptable way to meet the needs of the mode of administration. For example, the use of biomaterials and other polymers for drug delivery, as well the different techniques and models to validate a specific mode of administration, are disclosed in literature (Luo B and Prestwich G D, 2001; Cleland J L et al., 2001).

"Pharmaceutically acceptable" is meant to encompass any carrier, which does not interfere with the effectiveness of the biological activity of the active ingredient and that is not toxic to the host to which is administered. For example, for parenteral administration, the above active ingredients may be formulated in unit dosage form for injection in vehicles such as saline, dextrose solution, serum albumin and Ringer's solution. Carriers can be selected also from starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the various oils, including those of petroleum, animal, vegetable or synthetic origin (peanut oil, soybean oil, mineral oil, sesame oil).

Any accepted mode of administration can be used and determined by those skilled in the art to establish the desired blood levels of the active ingredients. For example, administration may be by various parenteral routes such as subcutaneous, intravenous, intradermal, intramuscular, intraperitoneal, intranasal, transdermal, rectal, oral, or buccal routes. The pharmaceutical compositions of the present invention can also be administered in sustained or controlled release dosage forms, including depot injections, osmotic pumps, and the like, for the prolonged administration of the polypeptide at a predetermined rate, preferably in unit dosage forms suitable for single administration of precise dosages.

Parenteral administration can be by bolus injection or by gradual perfusion over time. Preparations for parenteral administration include sterile aqueous or non-aqueous solutions, suspensions, and emulsions, which may contain auxiliary agents or excipients known in the art, and can be prepared according to routine methods. In addition, suspension of the active compounds as appropriate oily injection suspensions may be administered. Suitable lipophilic solvents or vehicles include fatty oils, for example, sesame oil, or synthetic fatty acid esters, for example, sesame oil, or synthetic fatty acid esters, for example, ethyl oleate or triglycerides. Aqueous injection suspensions that may contain substances increasing the viscosity of the suspension include, for example, sodium carboxymethyl cellulose, sorbitol, and/or dextran. Optionally, the suspension may also contain stabilizers. Pharmaceutical compositions include suitable solutions for administration by injection, and contain from about 0.01 to 99.99 percent, preferably from about 20 to 75 percent of active compound together with the excipient.

It is understood that the dosage administered will be dependent upon the age, sex, health, and weight of the recipient, kind of concurrent treatment, if any, frequency of treatment, and the nature of the effect desired. The dosage will be tailored to the individual subject, as is understood and determinable by one of skill in the art. The total dose required for each treatment may be administered by multiple doses or in a single dose. The pharmaceutical composition of the present invention may be administered alone or in conjunction with other therapeutics directed to the condition, or directed to other symptoms of the condition. Usually a daily dosage of active ingredient is comprised between 0.01 to 100 milligrams per kilogram of body weight per day. Ordinarily 1 to 40 milligrams per kilogram per day given in divided doses or in sustained release form is effective to obtain the desired results. Second or subsequent administrations can be performed at a dosage, which is the same, less than, or greater than the initial or previous dose administered to the individual.

A further aspect of this invention relates to compositions and methods for detecting or dosing a polypeptide or nucleic acid of this invention in a sample. Such compositions include, for instance, any specific ligand of a polypeptide of this invention, such as an antibody (or a fragment or derivative thereof); or any specific nucleic acid probes or primers.

In this regard, a further object of this invention is an antibody, or a fragment or derivative thereof, that selectively binds a human G-CSF polypeptide variant as disclosed above. In a more specific embodiment, the antibody, fragment or derivative thereof selectively binds an epitope comprising (or comprised in) amino acid residues 99-103 of SEQ ID NO: 4, SVA12 (LQLME), amino acid residues 99-103 of SEQ NO:2, SVW10 (LQLGL) and amino acid residues 63-67 of SEQ ID NO: 8, SVD09 EKLLC).

Within the context of this invention, the term "selective" binding indicates that the antibodies preferentially bind the target polypeptide or epitope, i.e., with a higher affinity than any binding to any other antigen or epitope. In other words, binding to the target polypeptide can be discriminated from non-specific binding to other antigens.

It is preferred that the antibodies (or a fragments or derivatives thereof) according to the present invention exhibit binding affinity (Ka) to the target polypeptide or epitope of $10^6$ $M^{-1}$ or greater, preferably $10^7 M^{-1}$ or greater, more preferably $10^8$ $M^{-1}$ or greater and most preferably $10^9$ $M^{-1}$ or greater. The binding affinity of an antibody can be readily determined by one of ordinary skill in the art, for example, by Scatchard analysis (Scatchard G., Ann NY Acad. Sci. 51: 660-672, 1949).

Antibodies of this invention may be monoclonal or polyclonal antibodies, or fragments or derivative thereof having substantially the same antigen specificity. The term fragment includes any binding portion of an antibody, such as Fab, F(ab')2, CDR domains, etc. Derivatives include human or humanized antibodies, polyfunctional antibodies, single-chain antibodies (e.g., ScFv), diabodies, monobodies etc. Methods for producing antibodies, fragments or derivatives thereof are well known in the art, including immunization of an animal and collection of serum (polyclonal) or spleen cells (to produce hybridomas by fusion with appropriate cell lines).

"Single-chain antibodies" are fragments of an antibody comprising the VH and VL domains of said antibody, wherein these domains are present in a single polypeptide chain. Preferably, the Fv polypeptide further comprises a polypeptide linker between the VH and VL domains which enables the single-chain antibody molecule to form the desired structure for antigen binding. For a review of single-chain antibody molecules, see, Pluckthun in The Pharmacology of Monoclonal Antibodies, Vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). Preferably, by using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

The term "monobodies" as used herein, refers to antigen binding molecules with a heavy chain variable domain and no light chain variable domain. A monobody can bind to an antigen in the absence of light chain and typically has three CDR regions designated CDRH1, CDRH2 and CDRH3. Monobodies include "camelid monobodies" obtained from a source animal of the camelid family, including animals with feet with two toes and leathery soles. Animals in the camelid family include camels, llamas, and alpacas. It has been reported that camels (*Camelus dromedaries* and *Camelus bactrianus*) often lack variable light chain domains when material from their serum is analyzed, suggesting that sufficient antibody specificity and affinity can be derived form VH domains (three CDR loops) alone. Monobodies also include modified VH from various animal sources, in particular mammals (for example mouse, rat, rabbit, horse, donkey, bovine or human), which can bind to an antigen in the absence of VL. Preferably, the VH is modified in positions at the VL interface to provide for binding of the VH to antigen in absence of the VL. Davies and Riechmann have for example demonstrated that "camelized monobodies" with high affinity (binding affinity (Ka) to the target polypeptide of $10^7$ $M^{-1}$ or greater) and high specificity can be generated (Davies & Riechmann, 1995, Biotechnology (NY), 13(5):475-9). Non-specific binding of the VH through its interface for the light chain variable domain (VL) was prevented through three mutations (G44E, L45R and W47G) in this interface. These mutations were introduced to mimic camelid antibody heavy chains naturally devoid of light chain partners.

Methods of producing polyclonal antibodies from various species, including rodents, primates and horses, have been described for instance in Vaitukaitis et al. (J Clin Endocrinol Metab. 33 (1971) p. 988). Briefly, the antigen is combined with an adjuvant (e.g., Freund's adjuvant) and administered to an animal, typically by sub-cutaneous injection. Repeated injections may be performed. Blood samples are collected and immunoglobulins or serum are separated.

Methods of producing monoclonal antibodies may be found, for instance, in Harlow et al (Antibodies: A laboratory Manual, CSH Press, 1988) or in Kohler et al (Nature 256 (1975) 495), incorporated therein by reference. Briefly, these methods comprise immunizing an animal with the antigen, subsequently recovering spleen cells and fusing these cells with immortalized cells, such as myeloma cells, to produce hybridomas. Hybrodimas producing the desired monoclonal antibodies can be selected by limit dilutions. Antibodies may also be produced by selection of combinatorial libraries of immunoglobulins, as disclosed for instance in Ward et al (Nature 341 (1989) 544).

The antibodies may be coupled to heterologous moieties, such as toxins, labels, drugs or other therapeutic agents, covalently or not, either directly or through the use of coupling agents or linkers.

Antibodies of this invention may be used for detecting, dosing, purifying or neutralizing G-CSF polypeptide variants of this invention. In a particular aspect, the invention thus resides in a method of detecting or dosing a G-CSF polypeptide variant as defined above in a sample, comprising contacting such a sample with an antibody, fragment or derivative thereof as disclosed above, and determining the formation or dosing the (relative) quantity of an immune complex. The sample may be for instance any biological fluid, such as blood, plasma, serum, etc., optionally diluted and/or treated. The antibody, fragment or derivative thereof may be in suspension or immobilized on a support. The presence or amount of immune complexes may be determined by any technique known per se in the art, e.g., by ELISA, RIA, etc., e.g., using reporter antibodies, labelled antibodies, etc.

Another aspect of this invention is a nucleic acid probe, wherein said probe selectively hybridizes to a nucleic acid as defined above or the complementary strand thereof. Probes denote a defined nucleic acid segment (or nucleotide analog segment, e.g., polynucleotide as defined herein) which can be used to identify a specific polynucleotide sequence present in samples, said nucleic acid segment comprising a nucleotide sequence complementary of the specific polynucleotide sequence to be identified. Probes of this invention typically comprise single-stranded nucleic acids of between 12 to 600 nucleotides in length, for instance of between 12 and 500, more preferably of between 15 and 400, typically of between 20 and 300. The sequence of the probes can be derived from the sequences of the G-CSF polypeptide variants gene sequence. The probe may contain nucleotide substitutions and/or chemical modifications, e.g., to increase the stability of hybrids or to label the probe. Typical examples of labels include, without limitation, radioactivity, fluorescence, luminescence, etc.

A further aspect of this invention is a nucleic acid primer that can be used to amplify at least a distinctive fragment of a nucleic acid molecule encoding a G-CSF polypeptide variant as defined above. A "primer" denotes a specific oligonucleotide sequence which is complementary to a target nucleotide sequence and used to hybridize to the target nucleotide sequence. A primer serves as an initiation point for nucleotide polymerization catalyzed by either DNA polymerase, RNA polymerase or reverse transcriptase. Typical primers of this invention are single-stranded nucleic acid molecules of about 6 to 50 nucleotides in length, more preferably of about 8 to about 40 nucleotides in length. The sequence of the primer can be derived directly from the sequence of the target nucleic acid molecule. Perfect complementarity between the primer sequence and the target gene is preferred, to ensure high specificity. However, certain mismatch may be tolerated.

Particular nucleic acid primers are able to specifically hybridize with a portion of the G-CSF variant nucleic acid that either flanks or encodes a distinctive fragment of such polypeptide variants. Specific examples of primers of this invention are disclosed below:

```
CSF03-SVA12 specific primers:
CSF3-F:
                                        (SEQ ID NO: 14)
AGCCTGCAGCCCAGCCCCACCCAGA CSF3-R:
                                        (SEQ ID NO: 15)
TAAATACATGGGATGGGGAGGGCTT, spF1:
                                        (SEQ ID NO: 16)
AGCCAGGCCCTGCAGCTGATGGAAG, Sc2476.R:
                                        (SEQ ID NO: 17)
TCAATGGTGATGGTGATGGTGGGGCTGGGCAAGGTGGCGTA CSF03-SVF10 specific primers:
CSF3-F:
                                        (SEQ ID NO: 18)
AGCCTGCAGCCCAGCCCCACCCAGA, CSF3-R:
                                        (SEQ ID NO: 19)
TAAATACATGGGATGGGGAGGGCTT, SVF10-spF1:
                                        (SEQ ID NO: 20)
GCCAGGCCCTGCAGCTGGGGCTCCT, Sc2476.R:
                                        (SEQ ID NO: 21)
TCAATGGTGATGGTGATGGTGGGGCTGGGCAAGGTGGCGTA CSF03-SVD09 specific primers:
CSF3-F:
                                        (SEQ ID NO: 22)
AGCCTGCAGCCCAGCCCCACCCAGA, CSF3-R:
                                        (SEQ ID NO: 23)
TAAATACATGGGATGGGGAGGGCTT, SVD09-spF1:
                                        (SEQ ID NO: 24)
GCGCTCCAGGAGAAGCTGCTGTGCC, Sc2476.R:
                                        (SEQ ID NO: 25)
TCAATGGTGATGGTGATGGTGGGGCTGGGCAAGGTGGCGTA CSF03-SVH11 specific primers:
CSF3-F:
                                        (SEQ ID NO: 26)
AGCCTGCAGCCCAGCCCCACCCAGA -continued
CSF3-R:
                                        (SEQ ID NO: 27)
TAAATACATGGGATGGGGAGGGCTT, Sc2476.FQ:
                                        (SEQ ID NO: 28)
AGCAGGCTTCGCCACCATGGCTGGACCTGCCAC SP.CSF3.H11.speR1:
                                        (SEQ ID NO: 29)
CATTCCCAGTTCTTCCATCAGCTGC
```

A further aspect of this invention thus resides in the use of a primer or probe as disclosed above to detect or diagnose the presence of a nucleic acid encoding a G-CSF variant of this invention in a sample. The method can be carried out according to techniques well know in the art, such as by contacting a sample with a probe as defined above under conditions allowing hybridisation to occur, and determining the presence of a hybrid; or by contacting a sample with a primer as defined above under conditions allowing nucleic acid amplification, and determining the presence of an amplification product.

Further aspects and advantages of the present invention will be disclosed in the following examples, which should be considered as illustrative only, and do not limit the scope of this application.

EXAMPLES

A. Purification of G-CSF Polypeptide Variants

The G-CSF variants were identified by extensive sequencing experiments from human cDNA libraries using commercially available kits. The sequencing and cloning were performed as described below, by first producing a pool and then reconstructing and cloning the full length coding sequences.

1. Production of Pool: SMART cDNA Synthesis

This amplification kit provides a novel method for performing both 5'- and 3'-rapid amplification of cDNA ends (RACE).

a) First-Strand cDNA Synthesis

Kit No 634914 (Clontech)

1—Mix preparation:
  0.5 µl RNA sample
  1 µl 3' SMART CDSPrimer II A (10 µM)
  1 µl SMART II A Oligonucleotide (10 µm)
  2.5 µl Deionized H2O 2—Mix contents and spin the tube briefly in a microcentrifuge 3—Incubate at 72° c. for 2 min 4—Cool the tube on ice for 2 min 5—Add the following to each reaction tube:
  2 µl 5× First-Strand Buffer
  1 µl DTT (20 mM)
  1 µl 50× dNTP (10 mM)
  1 µl PowerScript Reverse Transcriptase 6—Incubate the tubes at 42° C. for 1 hour 7—Add 190 µl of TE 1× (pH 7.5)

8—Incubate at 72° C. 7 min

9—Stock at −20° C.

b) Advantage-GC2 PCR Protocol

Complete kit for efficient, accurate, and convenient amplification of GC-rich templates. Kit ref. 639119 Clontech 1—Mix preparation:
  29 μl H2O
  10 μg 5×GCX 2 PCR buffer
  5 μl GC Melt (5M)
  2 μl Nested universal primer A 10 mM
  1 μl 50× dNTP (10 mM each)
  1 μl Advantage-GC Pol. Mix 2—Add 2 μl of the product obtain in step a)

3—PCR reaction:

| | | |
|---|---|---|
| 94° C. | 1 min | 1 cycle |
| 94° C. | 15 sec | |
| 65° C. | 5 sec | 20 cycles |
| 68° C. | 12 min | |
| 68° C. | 12 min | 1 cycle |

4—Tube for using: 0.4 ng/μl by tissue.

2. Cloning Method for Reconstruction

Gateway (Invitrogen) is a universal cloning technology based on the site-specific recombination properties of bacteriophage lambda (Landy, 1989). This technology provides a rapid and highly efficient way to move DNA sequences into multiple vector systems (pDONR201 (11798-014)) for functional analysis and protein expression.

a) First PCR

1—Mix composition

| | |
|---|---|
| 5 μl of reconstruction product | |
| 45 μl H2O | |
| 5 μl Buffer "Taq + Precision" 10X | ref. 600-211 Stratagène |
| 0.4 μl dNTP 25 mM | ref. 10297-018 Invitrogen |
| 1 μl primers at 10 μM each | named Sc****.F+ and Sc****.R |
| 0.25 μl Taq + Precision | ref. 600-211 Stratagène |
| 2.5 μl DMSO 100% | ref 15,453-8 sigma |

2—PCR cycles:

| | | |
|---|---|---|
| 94° C. | 1 min | 1 cycle |
| 94° C. | 40 sec | |
| 45° C. | 40 sec | 3 cycles |
| 72° C. | 1 min | |
| 94° C. | 40 sec | |
| 55° C. | 40 sec | 9 cycles |
| 72° C. | 1 min | |
| 72° C. | 5 min | |
| 4° C. | to finish | | b) Second PCR
1-Mix composition:

```
10 μl of PCR1 product 31.5 μl H2O
```

| | |
|---|---|
| 4 μl Buffer "Taq + Precision" 10X | ref. 600-211 Stratagène |
| 0.32 μl dNTP 25 mM | ref. 10297-018 Invitrogen |

4 μl primers GAT-5'
GGGGACAAGTTTGTACAAAAAAGCAGGCTTCGCCACCATG
GAT-3' (SEQ ID NO: 30)
GGGGACCACTTTGTACAAGAAAGCTGGGTTTCAATGGTGATG
(SEQ ID NO: 31)

| | |
|---|---|
| 0.2 μl Taq + Precision | ref. 600-211 Stratagène |

2—PCR cycles:

| | | |
|---|---|---|
| 94° C. | 1 min | 1 cycle |
| 94° C. | 40 sec | |
| 45° C. | 40 sec | 3 cycles |
| 72° C. | 1 min | |
| 94° C. | 1 min | |
| 94° C. | 40 sec | |
| 50° C. | 40 sec | 3 cycles |
| 72° C. | 1 min | |
| 94° C. | 40 sec | |
| 55° C. | 40 sec | 7 cycles |
| 72° C. | 1 min | |
| 72° C. | 5 min | |
| 4° C. | to finish | | c) BP reaction

1 - Mix composition:

| | |
|---|---|
| 1 μl of PRC2 product | |
| 4 μl TE10.1 | |
| 1 μl vector pDONR201(300 ng/μl) | ref 11798-014 Invitrogen |
| 2 μl buffer BP reaction 5X | ref 11789-013 Invitrogen |
| 2 μl BP clonase enzyme | ref 11789-013 Invitrogen |
| 2 - incubate 1hour at 25° c. | |
| 3 - add 1 μl of proteinase K | ref 1.24568 Merck |
| 4 - incubate 10 min at 37° C. | |
| 5 - stock at 4° C. | | d) Transformation

1—Mix composition:

| | |
|---|---|
| 1 μl of BP-reaction product | |
| 30 μl of ElectroMax DH10B cells | ref 18290-015 Invitrogen |
| Electroporation and add rapidly: | |
| 500 μl of SOC medium | ref (found with DH10B cells) |

2—incubate 1 hour at 37° C., under agitation

3—spread 30 μl on LB agar plate (+50 μg/ml of Kanamycine)

4—incubate 37° C. overnight

B. Tissue Distribution of the SVA12 and SVF10 Variants

The expression pattern of G-CSF variant mRNA was determined using RT-PCR analysis. The following cDNA templates was amplified using various primers, including variant-specific primers, to determine tissue expression of the variants.

cDNA Template:

Clontech tissue collection (HUMAN polyA RNA pancreas (636119), HUMAN polyA RNA skeletal muscle(636120), HUMAN polyA RNA small intestine(636125), HUMAN polyA RNA testis(636115), HUMAN polyA RNA liver (636101), HUMAN polyA RNA brain Whole (636102));

Invitrogen tissue collection, ref (Human total RNA, Normal adipose, D6005-01)

The template was amplified with the following primers:

```
.CSF03 specific primers
PCR1:
CSF3-F                              (SEQ ID NO: 14)
(AGCCTGCAGCCCAGCCCCACCCAGA),

CSF3-R                              (SEQ ID NO: 15)
(TAAATACATGGGATGGGGAGGGCTT),

PCR2:
Sc2476.FQ                           (SEQ ID NO: 28)
(AGCAGGCTTCGCCACCATGGCTGGACCTGCCAC),

Sc2476.R                            (SEQ ID NO: 17)
(TCAATGGTGATGGTGATGGTGGGGCTGGGCAAGGTGGCGTA)
```

502 BP (SVA12) and 604 by (SVF10) bands were observed for the variants versus 658 by for the wild type form.

```
.CSF03 (SVA12) variant specific primers:
PCR1:
CSF3-F                              (SEQ ID NO: 14)
(AGCCTGCAGCCCAGCCCCACCCAGA),

CSF3-R                              (SEQ ID NO: 15)
(TAAATACATGGGATGGGGAGGGCTT),

PCR2:
SVA12-spF1                          (SEQ ID NO: 24)
(AGCCAGGCCCTGCAGCTGATGGAAG),

Sc2476.R                            (SEQ ID NO: 17)
(TCAATGGTGATGGTGATGGTGGGGCTGGGCAAGGTGGCGTA)
```

A 201 by band was observed.

```
.CSF03 (SVF10) variant specific primers:
PCR1:
CSF3-F                              (SEQ ID NO: 14)
(AGCCTGCAGCCCAGCCCCACCCAGA),

CSF3-R                              (SEQ ID NO: 15)
(TAAATACATGGGATGGGGAGGGCTT),

PCR2:
SVF10-spF1                          (SEQ ID NO: 20),
(GCCAGGCCCTGCAGCTGGGGCTCCT)

Sc2476.R                            (SEQ ID NO: 17)
(TCAATGGTGATGGTGATGGTGGGGCTGGGCAAGGTGGCGTA)
```

A 302 bp band was observed.

For each tissue, the size and DNA concentration of each band were compared. The tissue distribution of the 2 isoforms was analyzed by migration on Agilent Bioanalyzer and the pattern was found not to be similar between the three forms (See Tables 1 and 2, and FIG. 3).

In small intestine, the normal form is present at 27%, and 100% for the SVA12 variant, and SF10 variant is not present in this tissue. In normal adipose, only the SVA12 variant is present. The particular distribution of SVA12 suggests a particular utility of this variant for treating adipose-related disorders, such as for example obesity and diabetes. SVA12 also may be particularly useful in the treatment of inflammations of the intestine, in particular the treatment of inflammations of the small intestine, the treatment of Crohn's disease, and/or the treatment of colitis ulcerosa.

The SF10 variant may be particularly useful in the treatment of inflammatory or proliferative diseases of the brain, testis, pancreas and skeletal muscle.

C. Tissue Distribution of the SVD09 and SVH11 Variants

The regional pattern of the SVD09 and SVH11 variant mRNA was determined using RT-PCR analysis.

The Following cDNA Template:

Clontech tissue collection, (HUMAN polyA RNA pancreas (636119), HUMAN polyA RNA skeletal muscle (636120), HUMAN polyA RNA small intestine (636125), HUMAN polyA RNA testis (636115), HUMAN polyA RNA liver (636101), HUMAN polyA RNA brain Whole (636102)); Invitrogen tissue collection, ref (Human total RNA, Normal adipose, lot A5040004));

was amplified with CSF03 specific primers

```
PCR1:
CSF3-F                              (SEQ ID NO: 14)
(AGCCTGCAGCCCAGCCCCACCCAGA),

CSF3-R                              (SEQ ID NO: 15)
(TAAATACATGGGATGGGGAGGGCTT),

PCR2:
Sc2476.FQ                           (SEQ ID NO: 28)
(AGCAGGCTTCGCCACCATGGCTGGACCTGCCAC),

Sc2476.R                            (SEQ ID NO: 17)
(TCAATGGTGATGGTGATGGTGGGGCTGGGCAAGGTGGCGTA)
```

627 by SVD09 and 504 by for SVH11 bands were observed for the variants versus 651 by for the wild type form.

```
PCR1:
CSF3-F                              (SEQ ID NO: 14)
(AGCCTGCAGCCCAGCCCCACCCAGA),

CSF3-R                              (SEQ ID NO: 15)
(TAAATACATGGGATGGGGAGGGCTT),

PCR2:
SVD09-spF1                          (SEQ ID NO: 24)
GCGCTCCAGGAGAAGCTGCTGTGCC

Sc2476.R                            (SEQ ID NO: 17)
TCAATGGTGATGGTGATGGTGGGGCTGGGCAAGGTGGCGTA
```

A 441 by band was observed.

```
PCR1:
CSF3-F                              (SEQ ID NO: 14)
AGCCTGCAGCCCAGCCCCACCCAGA

CSF3-R                              (SEQ ID NO: 15)
TAAATACATGGGATGGGGAGGGCTT,

PCR2:
Sc2476.FQ                           (SEQ ID NO: 28)
AGCAGGCTTCGCCACCATGGCTGGACCTGCCAC

SP.CSF3.H11.speR1                   (SEQ ID NO: 29)
CATTCCCAGTTCTTCCATCAGCTGC
```

A 336 bp band was observed.

For each tissue, the size and DNA concentration of each band were compared. Tissue distribution of the 2 isoforms was analyzed by migration on Agilent Bioanalyzer (See Tables 3 and 4, FIG. 4).

The results show that, in normal adipose, the wild type form is not present, and the variant form SVH11 is the most abundantly expressed. The particular distribution of SVH11 suggests a particular utility of this variant for treating adipose-related disorders, such as for example obesity and diabetes.

The variant form SVD09 is more abundant in small intestine, brain and pancreas. Thus, the SVD09 variant may be particularly useful in the treatment of inflammatory or proliferative diseases of the small intestine, brain and/or pancreas. SVD09 may be particularly useful in the treatment of inflammations of the intestine, in particular the treatment of inflammations of the small intestine, the treatment of Crohn's disease, and/or the treatment of colitis ulcerosa.

D. Biological Activity of the Variants

The biological activity of the polypeptides of this invention can be verified using several biological assays that are known per se in the art. The polypeptide can be injected directly (sc, ip, iv) in the animal or delivered using, e.g., FAST TRACK technologies (EP 04405494.8).

Assay 1:

G-CSF has emerged as the most widely used mobilizing agent in clinical studies employing stem cell mobilization (Schmitz et al. (1995) Primary transplantation of allogeneic peripheral blood progentior cells mobilized by filgrastim (granulocyte colony stimulating factor). Blood 85, 1666-1672). In addition, the importance of G-CSF in neutrophil production has been clearly demonstrated by the generation of mice deficient in either G-CSF or the G-CSF receptor. These mice are chronically neutropenic, showing a reduced number of mature neutrophils in the blood (Lieschke et al (1992) Physiologic role of G-CSF: insights from in vivo studies. Mol. Biol. Of Haematopoesis 2, 201-216; Liu et al (1995) Impaired production and increased apoptosis of neutrophils in G-CSF recipient deficient mice. Immunity 5, 491-501).

We have set up an assay that is based on this ability of G-CSF to mobilize hematoprogentior cells from the bone marrow. The assay can be conducted in a POC model, in which G-CSF induces an increase in white blood cells and neutrophil numbers in the circulating blood. This increase in cell recruitment can be measured either by coulter or alternatively, neutrophil recruitment may be measured by FACS analysis based on particular cell markers such as CD3 and/or CD19 (Velders et al. (2002) Enhancement of G-CSF-induced stem cell mobilization by antibodies against b2 integrins LFA-1 and Mac-1. Transplantation 100, 327-333).

G-CSF activity may also be assessed by measuring SDF1α levels (e.g., in the blood or bone marrow). SDF-1 (a chemokine) decreases in bone marrow 1 to 5 days upon injection of G-CSF and increases in the circulating blood. SDF1α levels can be measured using any known techniques, such as by ELISA (Petit et al (2002) G-CSF induced stem cell mobilization by decreasing bone marrow SDF-1 and upregulating CXCR4. Nature Immunology 3, 687-694).

Assays 2:

It was recently shown that not only neutrophils and their precursors but also monocytes are target cells for G-CSF. Functional receptors for G-CSF are expressed on monocytes and they react to G-CSF with an attenuated release of pro-inflammatory cytokines TNF-α, IL1-β and IL-12 (Boneberg and Hartung (2002) G-CSF attenuates LPS-stimulated IL-β release via suppressed processing of proIL1-β, whereas TNF-α release is inhibited on the level of pro-TNFα formation. Eur. J. Immunolgy 32, 1717-1725; Boneberg and Hartung (2002) Molecular aspects of anti-inflammatory action of G-CSF. Inflammation Research 51, 119-128).

G-CSF anti-inflammatory activity may be determined in LPS stimulated cells or animals. Such an assay may be conducted in vitro, with LPS stimulated (human) PMBCs and purified immune cell subtypes, or in vivo, e.g., in LPS stimulated mice. Upon administration of a G-CSF polypeptide, the decrease in IL1β, TNFα, IL12 and/or IL18 may be assessed as compared to control conditions

TABLE 1

|   | Protein | CF03 | | |
| --- | --- | --- | --- | --- |
| reconstruction | ORF (wild-type) | | 621 | |
|  | ORF (variant) | 465 | | 567 |
|  | PCR size norm prot | | 658 | |
|  | PCR size var prot | 502 | | 604 |
|  | EXT | 423-H12 (SVA12) | | 423-F11 (SVF10) |
|  | AGILENT | DNA (1000) dilution 1/21 | | DNA (1000) dilution 1/21 |
|  |  | NORM | var1 | NORM var2 |
|  | pool1 (size, conc) | 689 (3) | | 689 (3) |
|  | pool2 (size, conc) | 686 (3) | | 686 (3) |
|  | small intestine (size, conc) | 690 (0, 85) | | 690 (0, 85) |
|  | normal adipose (size, conc) | | | |
|  | brain (size, conc) | 694 (0, 53) | | 694 (0, 53) |
|  | testis (size, conc) | 695 (0, 94) | | 695 (0, 94) |
|  | liver (size, conc) | | | |
|  | pancreas (size, conc) | 703 (0, 71) | | 703 (0, 71) |
|  | squeletal muscle (size, conc) | 705 (3, 1) | | 705 (3, 1) |
| Specific |  | var1 (SVA12) | | var2 (SVF10) |
|  | size pcr prot var | 201 | | 302 |
|  | AGILENT | (DNA500) dilution 1/15 | | (DNA500) dilution 1/5 |
|  | pool1 (size, conc) | 204 (2, 8) | | 302 (11, 4) |
|  | pool2 (size, conc) | 203 (0, 86) | | 302 (13, 5) |
|  | small intestine (size, conc) | 204 (2, 5) | | |
|  | normal adipose (size, conc) | 205 (0, 92) | | |
|  | Brain (size, conc) | 205 (0, 75) | | 304 (11, 2) |
|  | Testis (size, conc) | 206 (1, 2) | | 305 (19, 5) |
|  | Liver (size, conc) | | | |
|  | Pancreas (size, conc) | 207 (1, 2) | | 306 (16, 3) |
|  | squeletal muscle (size, conc) | 207 (1, 1) | | 307 (14, 2) |

TABLE 2

|  | NOR % | SVA12 | SVF10 |
|---|---|---|---|
| small intestine | 27 | 100 | 0 |
| normal adipose | 0 | 37 | 0 |
| brain | 17 | 30 | 57 |
| testis | 30 | 48 | 100 |
| pancreas | 23 | 48 | 84 |
| squeletal muscle | 100 | 44 | 74 |

TABLE 3

| | | Protein | CSF3_HUMAN | |
|---|---|---|---|---|
| reconstruction (cloning PCR 1) | | ORF (wt) | 621 | |
| | | ORF (variant) | 597 SVD09-474 SVH11 | |
| | | size pcr prot norm | 658 | |
| | | size pcr prot var | 627 SVD09 504 SVH11 | |
| | | EXT | EXT: 267C03 (320-6-F06) | |
| | | AGILENT | DNA (1000) NORM. | |
| | | pool1 (size, conc) | 689 (3) | |
| | | small intestine (size, conc) | 690 (0, 85) | |
| | | normal adipose (size, conc) | | |
| | | brain (size, conc) | 694 (0, 53) | |
| | | testis (size, conc) | 695 (0, 94) | |
| | | liver (size, conc) | | |
| | | pancreas (size, conc) | 703 (0, 71) | |
| | | squeletal muscle (size, conc) | 705 (3, 1) | |
| specific (cloning PCR 2) | | | SP.CSF3_D09 | SP.CSF3_H11 |
| | | size pcr prot var | 441 (speF1) dil 1/3 | 336 (speR1) dil 1/10 |
| | | AGILENT | DNA (500) | DNA (500) |
| | | pool1 (size, conc) | 477 (24, 4) | 376 (2, 2) |
| | | small intestine (size, conc) | 471 (38, 1) | 371 (1, 1) |
| | | normal adipose (size, conc) | 465 (30, 7) | 378 (17, 1) |
| | | Brain (size, conc) | 472 (43) | 375 ((0, 96) |
| | | Testis (size, conc) | 467 (11, 7) | 371 (0, 91) |
| | | Liver (size, conc) | | |
| | | Pancreas (size, conc) | 468 (32, 5) | 374 (0, 54) |
| | | squeletal muscle (size, conc) | 472 (45, 8) | 373 (0, 69) |

TABLE 4

| % | wild type | SVD09 | SVH11 |
|---|---|---|---|
| pool1 | 97 | 53 | 13 |
| small intestine | 27 | 83 | 6 |
| normal adipose | 0 | 67 | 100 |
| brain | 17 | 94 | 6 |
| testis | 30 | 26 | 5 |
| pancreas | 23 | 71 | 3 |
| squeletal muscle | 100 | 100 | 4 |

The invention claimed is:

1. An isolated G-CSF polypeptide comprising:
   a) SEQ ID NO: 4; or
   b) a variant of SEQ ID NO: 4 containing up to 10 amino acid substitutions to SEQ ID NO: 4, wherein said variant binds a G-CSF receptor.

2. The isolated G-CSF polypeptide according to claim 1, wherein said polypeptide contains amino acid residues 99 to 103 of SEQ ID NO: 4 (LQLME).

3. The isolated G-CSF polypeptide according to claim 1, wherein said isolated G-CSF polypeptide comprises up to 10 amino acid substitutions to SEQ ID NO: 4 and binds a G-CSF receptor.

4. The isolated G-CSF polypeptide according to claim 3, wherein said isolated human G-CSF polypeptide retains helix A and/or helix B of human G-CSF.

5. The isolated G-CSF polypeptide according to claim 3, wherein said isolated human G-CSF polypeptide retains an IL-6 domain.

6. The isolated G-CSF polypeptide according to claim 1, wherein said isolated G-CSF polypeptide retains at least one biological activity selected from the increase of granulocytes in the blood stream, the mobilization of hematopoietic progenitor stem cells (HPCs), the anti-apoptotic activity, and/or the induction of anti-inflammatory factors.

7. The isolated G-CSF polypeptide according to claim 1, wherein said polypeptide comprises a fusion protein comprising an additional amino acid domain operably linked to:
   a) SEQ ID NO: 4; or
   b) a variant of SEQ ID NO: 4 comprising up to 10 amino acid substitutions to SEQ ID NO: 4, wherein said variant binds a G-CSF receptor.

8. The isolated G-CSF polypeptide according to claim 7, wherein said additional amino acid domain is operably linked to SEQ ID NO: 4.

9. The isolated G-CSF polypeptide according to claim 7, wherein said additional amino acid domain is operably linked to a variant of SEQ ID NO: 4 comprising up to 10 amino acid substitutions to SEQ ID NO: 4 and said variant binds a G-CSF receptor.

10. The isolated G-CSF polypeptide according to claim 8, wherein said additional amino acid domain is a signal peptide, a tag, a targeting peptide, the constant domain of an immunoglobulin molecule or a biologically active protein.

11. The isolated G-CSF polypeptide according to claim 9, wherein said additional amino acid domain is a signal peptide, a tag, a targeting peptide, the constant domain of an immunoglobulin molecule or a biologically active protein.

12. An isolated nucleic acid molecule encoding a polypeptide according to claim 1.

13. The isolated nucleic acid molecule according to claim 12, wherein said nucleic acid molecule is a cDNA molecule.

14. The isolated nucleic acid molecule according to claim 12, wherein said nucleic acid molecule encodes SEQ ID NO: 4.

15. The isolated nucleic acid molecule according to claim 12, wherein said nucleic acid molecule encodes a fusion protein comprising SEQ ID NO: 4 operably linked to an additional amino acid domain.

16. The isolated nucleic acid molecule according to claim 15, wherein said additional amino acid domain is a signal peptide, a tag, a targeting peptide, the constant domain of an immunoglobulin molecule or a biologically active protein.

17. The isolated nucleic acid molecule according to claim 14, wherein said nucleic acid comprises SEQ ID NO: 3.

18. The isolated nucleic acid molecule according to claim 12, wherein said nucleic acid molecule encodes a fusion protein comprising an additional amino acid domain operably linked to a variant of SEQ ID NO: 4 comprising up to 10 amino acid substitutions to SEQ ID NO: 4 and said variant binds a G-CSF receptor.

19. The isolated nucleic acid molecule according to claim 12, wherein said nucleic acid molecule encodes a variant of SEQ ID NO: 4 comprising up to 10 amino acid substitutions to SEQ ID NO: 4 and said variant binds a G-CSF receptor.

20. A vector comprising a nucleic acid molecule according to claim 12.

21. The vector according to claim 20, wherein said nucleic acid molecule encodes SEQ ID NO: 4.

22. The vector according to claim 20, wherein said nucleic acid molecule encodes a fusion protein comprising SEQ ID NO: 4 operably linked to an additional amino acid domain.

23. The vector according to claim 20, wherein said additional amino acid domain is a signal peptide, a tag, a targeting peptide, the constant domain of an immunoglobulin molecule or a biologically active protein.

24. The vector according to claim 21, wherein said nucleic acid comprises SEQ ID NO: 3.

25. The vector according to claim 20, wherein said nucleic acid molecule encodes a fusion protein comprising an additional amino acid domain operably linked to a variant of SEQ ID NO: 4 comprising up to 10 amino acid substitutions to SEQ ID NO: 4, wherein said variant binds a G-CSF receptor.

26. The vector according to claim 20, wherein said nucleic acid molecule encodes a variant of SEQ ID NO: 4 comprising up to 10 amino acid substitutions to SEQ ID NO: 4, wherein said variant binds a G-CSF receptor.

27. An isolated host cell comprising a vector according to claim 20.

28. The isolated host cell according to claim 27, wherein said host cell is a prokaryotic or eukaryotic cell.

29. The isolated host cell according to claim 27, wherein said nucleic acid molecule encodes SEQ ID NO: 4.

30. The isolated host cell according to claim 27, wherein said nucleic acid molecule encodes a fusion protein comprising SEQ ID NO: 4 operably linked to an additional amino acid domain.

31. The isolated host cell according to claim 27, wherein said additional amino acid domain is a signal peptide, a tag, a targeting peptide, the constant domain of an immunoglobulin molecule or a biologically active protein.

32. The isolated host cell according to claim 29, wherein said nucleic acid comprises SEQ ID NO: 3.

33. The isolated host cell according to claim 27, wherein said nucleic acid molecule encodes a fusion protein comprising an additional amino acid domain operably linked to a variant of SEQ ID NO: 4 comprising up to 10 amino acid substitutions to SEQ ID NO: 4, wherein said variant binds a G-CSF receptor.

34. The isolated host cell according to claim 27, wherein said nucleic acid molecule encodes a variant of SEQ ID NO: 4 comprising up to 10 amino acid substitutions to SEQ ID NO: 4, wherein said variant binds a G-CSF receptor.

35. A composition comprising a pharmaceutically acceptable carrier or diluent and a polypeptide comprising:
   a) SEQ ID NO: 4;
   b) a variant of SEQ ID NO: 4 comprising up to 10 amino acid substitutions to SEQ ID NO: 4, wherein said variant binds a G-CSF receptor; or c) a fusion protein comprising an additional amino acid domain operably linked to:
   i) SEQ ID NO: 4; or
   ii) a variant of SEQ ID NO: 4 comprising up to 10 amino acid substitutions to SEQ ID NO: 4, wherein said variant binds a G-CSF receptor.

36. A method of producing a polypeptide comprising culturing a recombinant host cell under conditions allowing expression of the nucleic acid molecule, and recovering the polypeptide produced, wherein said recombinant host cell comprises a nucleic acid encoding:
   a) SEQ ID NO: 4;
   b) a variant of SEQ ID NO: 4 comprising up to 10 amino acid substitutions to SEQ ID NO: 4, wherein said variant binds a G-CSF receptor; or
   c) a fusion protein comprising an additional amino acid domain operably linked to:
      i) SEQ ID NO: 4; or
      ii) a variant of SEQ ID NO: 4 comprising up to 10 amino acid substitutions to SEQ ID NO: 4, wherein said variant binds a G-CSF receptor.

37. A method of stimulating neutrophil production in a subject in need of comprising the administration of a composition comprising:
   a) SEQ ID NO: 4;
   b) a variant of SEQ ID NO: 4 comprising up to 10 amino acid substitutions to SEQ ID NO: 4, wherein said variant binds a G-CSF receptor; or
   c) a fusion protein comprising an additional amino acid domain operably linked to:
      i) SEQ ID NO: 4; or
      ii) a variant of SEQ ID NO: 4 comprising up to 10 amino acid substitutions to SEQ ID NO: 4, wherein said variant binds a G-CSF receptor.

38. A method of stimulating hematoprogenitor cell mobilization in a subject in need thereof comprising the administration of a composition comprising:
   a) SEQ ID NO: 4;
   b) a variant of SEQ ID NO: 4 comprising up to 10 amino acid substitutions to SEQ ID NO: 4, wherein said variant binds a G-CSF receptor; or
   c) a fusion protein comprising an additional amino acid domain operably linked to:
      i) SEQ ID NO: 4; or
      ii) a variant of SEQ ID NO: 4 comprising up to 10 amino acid substitutions to SEQ ID NO: 4, wherein said variant binds a G-CSF receptor.

* * * * *

UNITED STATES PATENT AND TRADEMARK OFFICE
CERTIFICATE OF CORRECTION

PATENT NO. : 7,790,174 B2
APPLICATION NO. : 11/722527
DATED : September 7, 2010
INVENTOR(S) : Catherine Gonthier et al.

It is certified that error appears in the above-identified patent and that said Letters Patent is hereby corrected as shown below:

Column 3,
Line 63, "normeutropenic" should read --nonneutropenic--.

Column 5,
Line 23, "CSF3_HUMAN_SV11," should read --CSF3_HUMAN_SVH11,--.

Column 6,
Line 65, "acidresidues" should read --acid residues--.

Column 7,
Line 32, "99:103" should read --99-103--.

Column 9,
Line 23, "heterolous" should read --heterologous--.

Column 10,
Line 64, "form viral" should read --from viral--.

Column 14,
Line 63, "SVD09 EKLLC)" should read --SVD09 (EKLLC)--.

Column 16,
Line 21, "Hybrodimas" should read --Hybridomas--.

Column 21,
Line 20, "604 by" should read --604 bp--.
Line 21, "658 by" should read --658 bp--.

Signed and Sealed this
Twenty-ninth Day of March, 2011

David J. Kappos
*Director of the United States Patent and Trademark Office*

Column 21,
Line 32, "(SEQ ID NO: 24)" should read --(SEQ ID NO: 16)--.
Line 37, "201 by" should read --201 bp--.

Column 22,
Line 30, "627 by SVD09 and 504 by for SVH11 bands were observed for the variants versus 651 by for the wild type form.

PCR1:"
should read

--627 bp SVD09 and 504 bp for SVH11 bands were observed for the variants versus 651 bp for the wild type form.

with CSF03_SVD09 variant specific primers:

PCR1:--.

Column 22,
Lines 46-48, "A 441 bp band was observed.

PCR1:"
should read

--A 441 bp band was observed.

And with CSF03_SVH11 variant specific primers:

PCR1:--.

Column 23,
Line 35, "hematoprogentior" should read --hematoprogenitor--.

Column 44,
Line 10, "variant hinds a" should read --variant binds a--.

Column 45,
Line 24, "in need of" should read --in need thereof--.

SEQUENCE LISTING

<160> NUMBER OF SEQ ID NOS: 31

<210> SEQ ID NO 1
<211> LENGTH: 570
<212> TYPE: DNA
<213> ORGANISM: Artificial sequence
<220> FEATURE:
<223> OTHER INFORMATION: CSF3_HUMAN_SVF10

<400> SEQUENCE: 1
atggctggac ctgccaccca gagccccatg aagctgatgg ccctgcagct gctgctgtgg     60

-continued

```
cacagtgcac tctggacagt gcaggaagcc accccctgg gccctgccag ctccctgccc    120
cagagcttcc tgctcaagtg cttagagcaa gtgaggaaga tccagggcga tggcgcagcg    180
ctccaggaga agctgtgtgc cacctacaag ctgtgccacc ccgaggagct ggtgctgctc    240
ggacactctc tgggcatccc ctgggctccc ctgagcagct gccccagcca ggccctgcag    300
ctggggctcc tgcaggccct ggaagggatc tcccccgagt tgggtcccac cttggacaca    360
ctgcagctgg acgtcgccga cttttgccacc accatctggc agcagatgga agaactggga    420
atggcccctg ccctgcagcc cacccagggt gccatgccgg ccttcgcctc tgctttccag    480
cgccgggcag gagggtcct agttgcctcc catctgcaga gcttcctgga ggtgtcgtac    540
cgcgttctac gccaccttgc ccagccctga                                      570
```

<210> SEQ ID NO 2
<211> LENGTH: 189
<212> TYPE: PRT
<213> ORGANISM: Artificial sequence
<220> FEATURE:
<223> OTHER INFORMATION: CSF3_HUMAN_SVF10

<400> SEQUENCE: 2

```
Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Cys Ala Thr Tyr Lys Leu Cys His Pro Glu Glu Leu Val Leu Leu
65                  70                  75                  80

Gly His Ser Leu Gly Ile Pro Trp Ala Pro Leu Ser Ser Cys Pro Ser
                85                  90                  95

Gln Ala Leu Gln Leu Gly Leu Leu Gln Ala Leu Glu Gly Ile Ser Pro
            100                 105                 110

Glu Leu Gly Pro Thr Leu Asp Thr Leu Gln Leu Asp Val Ala Asp Phe
        115                 120                 125

Ala Thr Thr Ile Trp Gln Gln Met Glu Glu Leu Gly Met Ala Pro Ala
    130                 135                 140

Leu Gln Pro Thr Gln Gly Ala Met Pro Ala Phe Ala Ser Ala Phe Gln
145                 150                 155                 160

Arg Arg Ala Gly Gly Val Leu Val Ala Ser His Leu Gln Ser Phe Leu
                165                 170                 175

Glu Val Ser Tyr Arg Val Leu Arg His Leu Ala Gln Pro
            180                 185
```

<210> SEQ ID NO 3
<211> LENGTH: 468
<212> TYPE: DNA
<213> ORGANISM: Artificial sequence
<220> FEATURE:
<223> OTHER INFORMATION: CSF3_HUMAN_SVA12

<400> SEQUENCE: 3

```
atggctggac ctgccaccca gagccccatg aagctgatgg ccctgcagct gctgctgtgg    60
cacagtgcac tctggacagt gcaggaagcc accccctgg gccctgccag ctccctgccc    120
```

```
cagagcttcc tgctcaagtg cttagagcaa gtgaggaaga tccagggcga tggcgcagcg    180
ctccaggaga agctgtgtgc cacctacaag ctgtgccacc ccgaggagct ggtgctgctc    240
ggacactctc tgggcatccc ctgggctccc ctgagcagct gccccagcca ggccctgcag    300
ctgatggaag aactgggaat ggcccctgcc ctgcagccca ccagggtgc catgccggcc     360 ttcgcctctg ctttccagcg ccgggcagga ggggtcctgg ttgcctccca tctgcagagc    420
ttcctggagg tgtcgtaccg cgttctacgc accttgccc agccctga                 468
```

<210> SEQ ID NO 4
<211> LENGTH: 155
<212> TYPE: PRT
<213> ORGANISM: Artificial sequence
<220> FEATURE:
<223> OTHER INFORMATION: CSF3_HUMAN_SVA12

<400> SEQUENCE: 4

```
Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Cys Ala Thr Tyr Lys Leu Cys His Pro Glu Glu Leu Val Leu Leu
65                  70                  75                  80

Gly His Ser Leu Gly Ile Pro Trp Ala Pro Leu Ser Ser Cys Pro Ser
                85                  90                  95

Gln Ala Leu Gln Leu Met Glu Glu Leu Gly Met Ala Pro Ala Leu Gln
            100                 105                 110

Pro Thr Gln Gly Ala Met Pro Ala Phe Ala Ser Ala Phe Gln Arg Arg
        115                 120                 125

Ala Gly Gly Val Leu Val Ala Ser His Leu Gln Ser Phe Leu Glu Val
    130                 135                 140

Ser Tyr Arg Val Leu Arg His Leu Ala Gln Pro
145                 150                 155
```

<210> SEQ ID NO 5
<211> LENGTH: 474
<212> TYPE: DNA
<213> ORGANISM: Artificial sequence
<220> FEATURE:
<223> OTHER INFORMATION: CSF3_HUMAN_SVH11

<400> SEQUENCE: 5

```
atggctggac tgccaccca gagccccatg aagctgatgg ccctgcagct gctgctgtgg     60
cacagtgcac tctggacagt gcaggaagcc accccctgg gccctgccag ctccctgccc    120
cagagcttcc tgctcaagtg cttagagcaa gtgaggaaga tccagggcga tggcgcagcg    180
ctccaggaga agctggtgag tgagtgtgcc acctacaagc tgtgccaccc cgaggagctg    240
gtgctgctcg gacactctct gggcatcccc tgggctcccc tgagcagctg ccccagccag    300
gccctgcagc tgatggaaga actgggaatg gcccctgccc tgcagccac ccagggtgcc    360 atgccggcct tcgcctctgc tttccagcgc cgggcaggag gggtcctggt tgcctcccat    420
ctgcagagct tcctggaggt gtcgtaccgc gttctacgcc accttgccca gccc         474
```

<210> SEQ ID NO 6
<211> LENGTH: 158
<212> TYPE: PRT
<213> ORGANISM: Artificial sequence
<220> FEATURE:
<223> OTHER INFORMATION: CSF3_HUMAN_SVH11

<400> SEQUENCE: 6

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Met Glu Glu Leu Gly Met Ala Pro
            100                 105                 110

Ala Leu Gln Pro Thr Gln Gly Ala Met Pro Ala Phe Ala Ser Ala Phe
        115                 120                 125

Gln Arg Arg Ala Gly Gly Val Leu Val Ala Ser His Leu Gln Ser Phe
130                 135                 140

Leu Glu Val Ser Tyr Arg Val Leu Arg His Leu Ala Gln Pro
145                 150                 155

<210> SEQ ID NO 7
<211> LENGTH: 597
<212> TYPE: DNA
<213> ORGANISM: Artificial sequence
<220> FEATURE:
<223> OTHER INFORMATION: CSF3_HUMAN_SVD09

<400> SEQUENCE: 7
atggctggac ctgccaccca gagccccatg aagctgatgg ccctgcagct gctgctgtgg      60
cacagtgcac tctggacagt gcaggaagcc accccctgg ccctgccag ctccctgccc      120 cagagcttcc tgctcaagtg cttagagcaa gtgaggaaga tccagggcga tggcgcagcg      180
ctccaggaga gctgctgtg ccaccccgag gagctggtgc tgctcggaca ctctctgggc      240
atcccctggg ctcccctgag cagctgcccc agccaggccc tgcagctggc aggctgcttg      300
agccaactcc atagcggcct tttcctctac caggggctcc tgcaggccct ggaagggatc      360
tcccccgagt gggtcccac cttggacgca ctgcagctgg acgtcgccga ctttgccacc      420
accatctggc agcagatgga agaactggga atggcccctg ccctgcagcc cacccagggt      480
gccatgccgg ccttcgcctc tgctttccag cgccgggcag gaggggtcct ggttgcctcc      540
catctgcaga gcttcctgga ggtgtcgtac cgcgttctac gccaccttgc ccagccc      597

<210> SEQ ID NO 8
<211> LENGTH: 199
<212> TYPE: PRT
<213> ORGANISM: Artificial sequence
<220> FEATURE:
<223> OTHER INFORMATION: CSF3_HUMAN_SVD09

<400> SEQUENCE: 8

```
Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
50                  55                  60

Leu Leu Cys His Pro Glu Glu Leu Val Leu Leu Gly His Ser Leu Gly
65                  70                  75                  80

Ile Pro Trp Ala Pro Leu Ser Ser Cys Pro Ser Gln Ala Leu Gln Leu
                85                  90                  95

Ala Gly Cys Leu Ser Gln Leu His Ser Gly Leu Phe Leu Tyr Gln Gly
            100                 105                 110

Leu Leu Gln Ala Leu Glu Gly Ile Ser Pro Glu Leu Gly Pro Thr Leu
        115                 120                 125

Asp Ala Leu Gln Leu Asp Val Ala Asp Phe Ala Thr Thr Ile Trp Gln
130                 135                 140

Gln Met Glu Glu Leu Gly Met Ala Pro Ala Leu Gln Pro Thr Gln Gly
145                 150                 155                 160

Ala Met Pro Ala Phe Ala Ser Ala Phe Gln Arg Arg Ala Gly Gly Val
                165                 170                 175

Leu Val Ala Ser His Leu Gln Ser Phe Leu Glu Val Ser Tyr Arg Val
            180                 185                 190

Leu Arg His Leu Ala Gln Pro
        195

<210> SEQ ID NO 9
<211> LENGTH: 207
<212> TYPE: PRT
<213> ORGANISM: Artificial sequence
<220> FEATURE:
<223> OTHER INFORMATION: CSF3_HUMAN

<400> SEQUENCE: 9

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Ala Gly Cys Leu Ser Gln Leu His
            100                 105                 110

Ser Gly Leu Phe Leu Tyr Gln Gly Leu Leu Gln Ala Leu Glu Gly Ile
        115                 120                 125

Ser Pro Glu Leu Gly Pro Thr Leu Asp Thr Leu Gln Leu Asp Val Ala
130                 135                 140

Asp Phe Ala Thr Thr Ile Trp Gln Gln Met Glu Glu Leu Gly Met Ala
145                 150                 155                 160
```

Pro Ala Leu Gln Pro Thr Gln Gly Ala Met Pro Ala Phe Ala Ser Ala
            165                 170                 175

Phe Gln Arg Arg Ala Gly Gly Val Leu Val Ala Ser His Leu Gln Ser
        180                 185                 190

Phe Leu Glu Val Ser Tyr Arg Val Leu Arg His Leu Ala Gln Pro
    195                 200                 205

<210> SEQ ID NO 10
<211> LENGTH: 204
<212> TYPE: PRT
<213> ORGANISM: Artificial sequence
<220> FEATURE:
<223> OTHER INFORMATION: CSF3_HUMAN

<400> SEQUENCE: 10

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Cys Ala Thr Tyr Lys Leu Cys His Pro Glu Glu Leu Val Leu Leu
65                  70                  75                  80

Gly His Ser Leu Gly Ile Pro Trp Ala Pro Leu Ser Ser Cys Pro Ser
                85                  90                  95

Gln Ala Leu Gln Leu Ala Gly Cys Leu Ser Gln Leu His Ser Gly Leu
            100                 105                 110

Phe Leu Tyr Gln Gly Leu Leu Gln Ala Leu Glu Gly Ile Ser Pro Glu
        115                 120                 125

Leu Gly Pro Thr Leu Asp Thr Leu Gln Leu Asp Val Ala Asp Phe Ala
    130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
            180                 185                 190

Val Ser Tyr Arg Val Leu Arg His Leu Ala Gln Pro
        195                 200

<210> SEQ ID NO 11
<211> LENGTH: 11
<212> TYPE: PRT
<213> ORGANISM: Artificial sequence
<220> FEATURE:
<223> OTHER INFORMATION: subsequence of a GCSF variant polypeptide

<400> SEQUENCE: 11

Cys Pro Ser Gln Ala Leu Gln Leu Met Glu Cys
1               5                   10

<210> SEQ ID NO 12
<211> LENGTH: 11
<212> TYPE: PRT
<213> ORGANISM: Artificial sequence
<220> FEATURE:
<223> OTHER INFORMATION: subsequence of a GCSF variant polypeptide -continued

<400> SEQUENCE: 12

Cys Pro Ser Gln Ala Leu Gln Leu Gly Leu Cys
1               5                   10

<210> SEQ ID NO 13
<211> LENGTH: 7
<212> TYPE: PRT
<213> ORGANISM: Artificial sequence
<220> FEATURE:
<223> OTHER INFORMATION: subsequence of a GCSF variant polypeptide

<400> SEQUENCE: 13

Cys Gln Glu Lys Leu Leu Cys
1               5

<210> SEQ ID NO 14
<211> LENGTH: 25
<212> TYPE: DNA
<213> ORGANISM: Artificial sequence
<220> FEATURE:
<223> OTHER INFORMATION: CSF03-SVA12 specific primers

<400> SEQUENCE: 14
agcctgcagc ccagccccac ccaga                                           25

<210> SEQ ID NO 15
<211> LENGTH: 25
<212> TYPE: DNA
<213> ORGANISM: Artificial sequence
<220> FEATURE:
<223> OTHER INFORMATION: CSF03-SVA12 specific primers

<400> SEQUENCE: 15
taaatacatg ggatggggag ggctt 25

<210> SEQ ID NO 16
<211> LENGTH: 25
<212> TYPE: DNA
<213> ORGANISM: Artificial sequence
<220> FEATURE:
<223> OTHER INFORMATION: CSF03-SVA12 specific primers

<400> SEQUENCE: 16
agccaggccc tgcagctgat ggaag 25

<210> SEQ ID NO 17
<211> LENGTH: 41
<212> TYPE: DNA
<213> ORGANISM: Artificial sequence
<220> FEATURE:
<223> OTHER INFORMATION: CSF03-SVA12 specific primers

<400> SEQUENCE: 17
tcaatggtga tggtgatggt ggggctgggc aaggtggcgt a 41

<210> SEQ ID NO 18
<211> LENGTH: 25
<212> TYPE: DNA
<213> ORGANISM: Artificial sequence
<220> FEATURE:
<223> OTHER INFORMATION: CSF03-SVF10 specific primers

<400> SEQUENCE: 18
agcctgcagc ccagccccac ccaga 25

```
<210> SEQ ID NO 19
<211> LENGTH: 25
<212> TYPE: DNA
<213> ORGANISM: Artificial sequence
<220> FEATURE:
<223> OTHER INFORMATION: CSF03-SVF10 specific primers

<400> SEQUENCE: 19
taaatacatg ggatggggag ggctt                                              25

<210> SEQ ID NO 20
<211> LENGTH: 25
<212> TYPE: DNA
<213> ORGANISM: Artificial sequence
<220> FEATURE:
<223> OTHER INFORMATION: CSF03-SVF10 specific primers

<400> SEQUENCE: 20
gccaggccct gcagctgggg ctcct                                              25

<210> SEQ ID NO 21
<211> LENGTH: 41
<212> TYPE: DNA
<213> ORGANISM: Artificial sequence
<220> FEATURE:
<223> OTHER INFORMATION: CSF03-SVF10 specific primers

<400> SEQUENCE: 21
tcaatggtga tggtgatggt ggggctgggc aaggtggcgt a                            41

<210> SEQ ID NO 22
<211> LENGTH: 25
<212> TYPE: DNA
<213> ORGANISM: Artificial sequence
<220> FEATURE:
<223> OTHER INFORMATION: CSF03-SVD09 specific primers

<400> SEQUENCE: 22
agcctgcagc ccagccccac ccaga                                              25

<210> SEQ ID NO 23
<211> LENGTH: 25
<212> TYPE: DNA
<213> ORGANISM: Artificial sequence
<220> FEATURE:
<223> OTHER INFORMATION: CSF03-SVD09 specific primers

<400> SEQUENCE: 23
taaatacatg ggatggggag ggctt                                              25

<210> SEQ ID NO 24
<211> LENGTH: 25
<212> TYPE: DNA
<213> ORGANISM: Artificial sequence
<220> FEATURE:
<223> OTHER INFORMATION: CSF03-SVD09 specific primers

<400> SEQUENCE: 24
gcgctccagg agaagctgct gtgcc                                              25

<210> SEQ ID NO 25
<211> LENGTH: 41
<212> TYPE: DNA
<213> ORGANISM: Artificial sequence
<220> FEATURE:
<223> OTHER INFORMATION: CSF03-SVD09 specific primers
```

```
<400> SEQUENCE: 25
tcaatggtga tggtgatggt ggggctgggc aaggtggcgt a                    41

<210> SEQ ID NO 26
<211> LENGTH: 25
<212> TYPE: DNA
<213> ORGANISM: Artificial sequence
<220> FEATURE:
<223> OTHER INFORMATION: CSF03-SVH11 specific primers

<400> SEQUENCE: 26
agcctgcagc ccagccccac ccaga                                      25

<210> SEQ ID NO 27
<211> LENGTH: 25
<212> TYPE: DNA
<213> ORGANISM: Artificial sequence
<220> FEATURE:
<223> OTHER INFORMATION: CSF03-SVH11 specific primers

<400> SEQUENCE: 27
taaatacatg ggatggggag ggctt                                      25

<210> SEQ ID NO 28
<211> LENGTH: 33
<212> TYPE: DNA
<213> ORGANISM: Artificial sequence
<220> FEATURE:
<223> OTHER INFORMATION: CSF03-SVH11 specific primers

<400> SEQUENCE: 28
agcaggcttc gccaccatgg ctggacctgc cac                             33

<210> SEQ ID NO 29
<211> LENGTH: 25
<212> TYPE: DNA
<213> ORGANISM: Artificial sequence
<220> FEATURE:
<223> OTHER INFORMATION: CSF03-SVH11 specific primers

<400> SEQUENCE: 29
cattcccagt tcttccatca gctgc                                      25

<210> SEQ ID NO 30
<211> LENGTH: 40
<212> TYPE: DNA
<213> ORGANISM: Artificial sequence
<220> FEATURE:
<223> OTHER INFORMATION: primer

<400> SEQUENCE: 30
ggggacaagt ttgtacaaaa aagcaggctt cgccaccatg                      40

<210> SEQ ID NO 31
<211> LENGTH: 42
<212> TYPE: DNA
<213> ORGANISM: Artificial sequence
<220> FEATURE:
<223> OTHER INFORMATION: primer

<400> SEQUENCE: 31
ggggaccact ttgtacaaga aagctgggtt tcaatggtga tg                   42
```